US009999786B2

(12) United States Patent
Yoshimizu et al.

(10) Patent No.: US 9,999,786 B2
(45) Date of Patent: Jun. 19, 2018

(54) RADIATION EMITTING APPARATUS, RADIATION THERAPY APPARATUS, AND COLLIMATOR DRIVE CONTROL METHOD

(71) Applicant: Accuthera Inc., Kawasaki, Kanagawa (JP)

(72) Inventors: Eiki Yoshimizu, Tokyo (JP); Atsuyuki Oyamada, Tokyo (JP)

(73) Assignee: ACCUTHERA INC., Kawasaki (JP)

( * ) Notice: Subject to any disclaimer, the term of this patent is extended or adjusted under 35 U.S.C. 154(b) by 0 days. days.

(21) Appl. No.: 15/649,641

(22) Filed: Jul. 14, 2017

(65) Prior Publication Data
US 2018/0028839 A1     Feb. 1, 2018

(30) Foreign Application Priority Data

Jul. 29, 2016    (JP) ................. 2016-150578

(51) Int. Cl.
*G21K 1/02*      (2006.01)
*A61N 5/10*      (2006.01)
*A61N 5/06*      (2006.01)

(52) U.S. Cl.
CPC ......... *A61N 5/1045* (2013.01); *A61N 5/1065* (2013.01); *A61N 5/1069* (2013.01); *A61N 2005/0632* (2013.01); *A61N 2005/1061* (2013.01); *A61N 2005/1062* (2013.01)

(58) Field of Classification Search
CPC ................ A61N 5/1065; A61N 1/1069; A61N 2005/0632; A61N 2005/1061; A61N 2005/1062; G21K 1/02
See application file for complete search history.

(56) References Cited

U.S. PATENT DOCUMENTS

| 5,278,886 | A | * | 1/1994 | Kobiki | ................. A61N 5/1049 378/151 |
|---|---|---|---|---|---|
| 7,856,086 | B2 | | 12/2010 | Tanabe | |
| 8,358,737 | B2 | | 1/2013 | Tanabe | |
| 8,731,142 | B2 | | 5/2014 | Tanabe et al. | |

(Continued)

FOREIGN PATENT DOCUMENTS

| JP | H05-188199 A1 | 7/1993 |
|---|---|---|
| JP | H08-190433 A1 | 7/1996 |

(Continued)

*Primary Examiner* — Mark R Gaworecki
(74) *Attorney, Agent, or Firm* — Isshiki International Law Office; Joseph P. Farrar, Esq.

(57) ABSTRACT

A radiation emitting apparatus includes a radiation source to generate radiation, a first collimator to define a maximum radiation field of the radiation; a second collimator to regulate the radiation field and direction of irradiation; a swing portion that swings in two directions orthogonal to each other; a displacement detector to detect displacement of the second collimator relative to a reference point; a drive mechanism to drive the swing portion; a control unit to control the drive mechanism; and a storage unit included in the control unit to store one or more parameters related to mechanical movement of the swing portion. The control unit generates feedforward control information based on an inputted target swing angle, a detected displacement, and the one or more parameters stored in the storage unit, and outputs a drive signal containing the feedforward control information to the drive mechanism.

15 Claims, 22 Drawing Sheets

(56) References Cited

U.S. PATENT DOCUMENTS

| | | | |
|---|---|---|---|
| 8,989,350 B2 | 3/2015 | Shibuya et al. | |
| 9,149,656 B2 | 10/2015 | Tanabe | |
| 2013/0336449 A1 | 12/2013 | Tanabe | |

FOREIGN PATENT DOCUMENTS

| | | |
|---|---|---|
| JP | 2006-201925 A1 | 8/2006 |
| JP | 4418888 B2 | 2/2010 |
| JP | 4650642 B2 | 3/2011 |
| JP | 5260572 B2 | 8/2013 |
| JP | 5338000 B2 | 11/2013 |
| JP | 5358849 B2 | 12/2013 |
| JP | 2014000128 A1 | 1/2014 |

\* cited by examiner

APPEARANCE OF RADIATION EMITTING APPARATUS

CONTINUOUS IRRADIATION IN MULTIPLE DIRECTIONS
BY TRACKING MOVING-BODY

CONFIGURATION EXAMPLE OF X-RAY RADIATION DEVICE

EXAMPLE OF COLLIMATOR DEVICE

FIG. 17

| NUMBER OF TIMES | 1 | 2 | 3 | 4 | 5 | 6 | 7 | 8 | 9 | 10 |
|---|---|---|---|---|---|---|---|---|---|---|
| FRICTION INFORMATION STORAGE UNIT [N·m·s/rad] | 1 | 2 | 3 | 4 | 5 | 3 | 3 | 3 | 3 | 3 |
| GAIN | 0.5 | 0.5 | 0.5 | 0.5 | 0.5 | 0.5 | 0.6 | 0.7 | 0.8 | 0.9 |
| MAXIMUM ANGLE ERROR [mrad] | 2.5 | 2 | 0.7 | 1.5 | 2 | 0.7 | 0.6 | 0.5 | 0.3 | 0.4 |

Columns 1–5: DETERMINE FRICTION PARAMETER
Columns 6–10: DETERMINE OPTIMAL GAIN PARAMETER

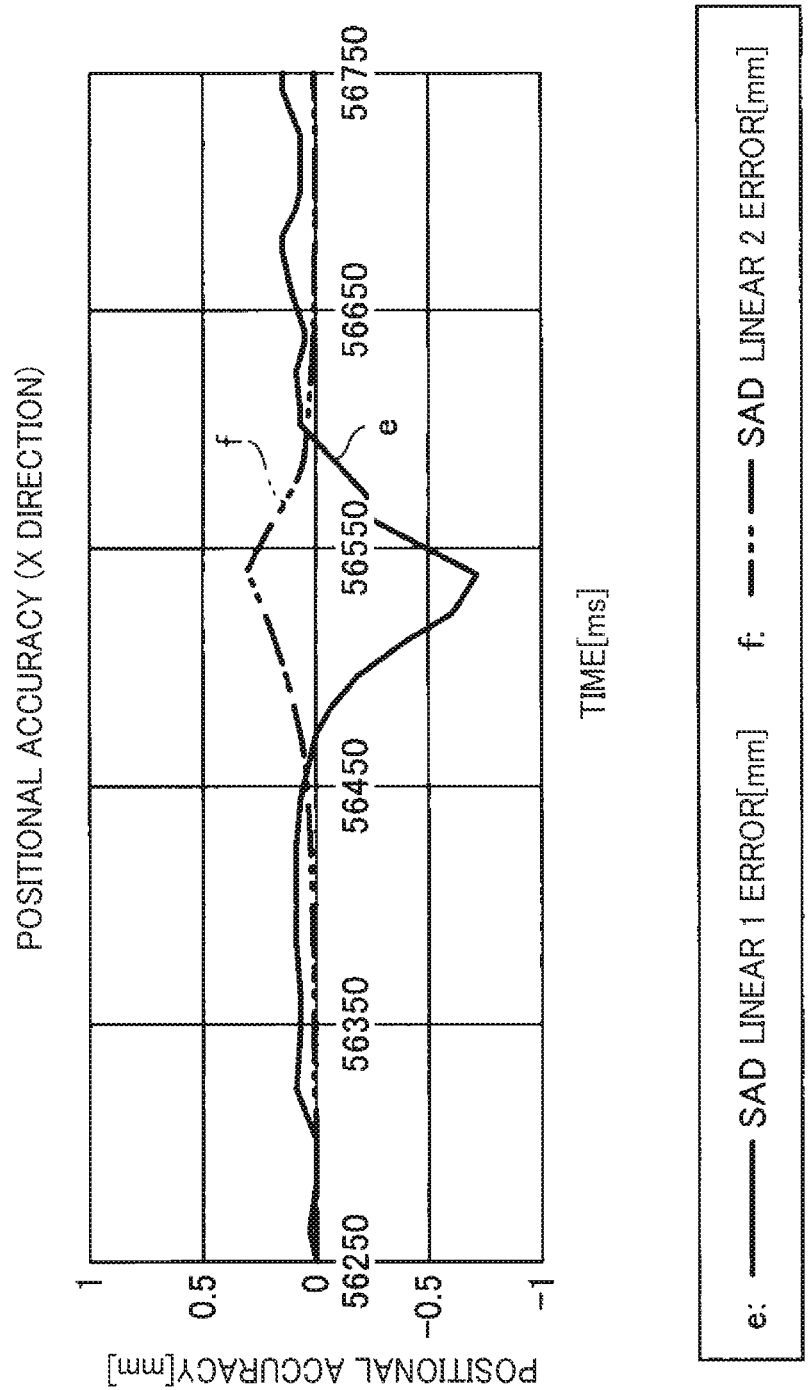

USE OF THIRD COLLIMATOR HAVING DIFFERENT RADIATION FIELD

RADIATION EMITTING APPARATUS, RADIATION THERAPY APPARATUS, AND COLLIMATOR DRIVE CONTROL METHOD

CROSS-REFERENCE TO RELATED APPLICATION

The present application claims priority pursuant to 35 U.S.C. § 119(a) from Japanese patent application number 2016-150578, filed on Jul. 29, 2016, the entire disclosure of which is incorporated by reference herein.

BACKGROUND

Technical Field

The present disclosure relates to a radiation emitting apparatus, a radiation therapy apparatus incorporating the radiation emitting apparatus, and a collimator drive control method employed by the radiation therapy apparatus to control the radiation emitting apparatus.

Related Art

In radiation (for example, X-ray) therapy, when an affected area of a radiation target is irradiated with X-rays, it is desirable to accurately irradiate abnormal cells, such as tumor cells, with X-rays, but not to irradiate normal cells as much as possible. However, since a tumor located close to the lungs or heart moves in a complex manner with breathing and heartbeat, dynamic position tracking performance is required.

Conventional irradiation methods include a method of irradiation with a radiation field including a motion range. In this case, in order to reduce the effects on normal cells, low-dose irradiation is carried out multiple times.

Another method is a targeting irradiation method in which irradiation is carried out at the timing of exhaling and inhaling in accordance with the motion of breathing. This method requires a medium margin in a radiation field, resulting in multiple treatments, and further requires lengthy treatment sessions.

Still another method is a method of tracking a tumor, using swinging movement of an X-ray head, from the irradiating position on a predetermined sphere. This type of radiation therapy apparatus drive method includes a method of calculating a feedforward operation amount based on a change in a post-correction target position and controlling a drive unit based on the feedforward operation amount. In this method, the drive unit is controlled so that a specific part is tracked after a radiation emitting apparatus has been gently moved.

In the conventional radiation therapy using swinging movement, a six-axis manipulator is used to change the direction of the entire X-ray head and track the motion of a tumor, etc., which results in insufficient tracking performance and irradiation accuracy. Further, the X-ray head is stopped at each irradiating position so that the swinging movement of the X-ray head is controlled and irradiation is carried out. Thus, a period of time for stabilizing vibrations in association with acceleration/deceleration of the X-ray head is necessary for each irradiation, and this requires a long treatment time.

Accordingly, the present disclosure provides a radiation emitting apparatus configured to track and irradiate a moving body quickly and accurately, and a collimator drive control technique.

SUMMARY

In order to achieve the above described object, parameters related to mechanical movement of a swing portion including a swing collimator are stored in a storage unit of a radiation emitting apparatus, and feedforward control information is generated to control drive of the swing portion.

In one aspect of this disclosure, a novel radiation emitting apparatus includes a radiation source to generate radiation, a first collimator to define a maximum radiation field of the radiation, a second collimator to regulate the radiation field and direction of irradiation, a swing portion, a displacement detector, a drive mechanism, a control unit, and a storage unit. The second collimator is disposed within the first collimator. The swing portion incorporates the second collimator to swing in two directions orthogonal to each other. The displacement detector detects displacement of the second collimator relative to a reference point. The drive mechanism drives the swing portion. The control unit generates feedforward control information to control the drive mechanism. The storage unit is included in the control unit and stores one or more parameters related to mechanical movement of the swing portion. The control unit generates the feedforward control information based on an inputted target swing angle, a detected displacement, and the one or more parameters stored in the storage unit, and outputs a drive signal containing the feedforward control information to the drive mechanism.

In another aspect of this disclosure, a collimator drive control method for the radiation emitting apparatus includes receiving inputted target swing angle information at the control unit; obtaining the displacement from the displacement detector; reading the parameter from the storage unit; generating, with the control unit, feedforward control information based on the target swing angle information, the displacement, and the one or more parameters stored in the storage unit; and outputting, from the control unit, a drive signal containing the feedforward control information to the drive mechanism to drive the swing portion.

According to the present disclosure, it is implemented to track and irradiate a moving body quickly and accurately.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 17 illustrates a specific example of FF control parameters.

FIG. 19 is a diagram illustrating grounds for correcting tracking using FF control.

DETAILED DESCRIPTION

Figure 1:
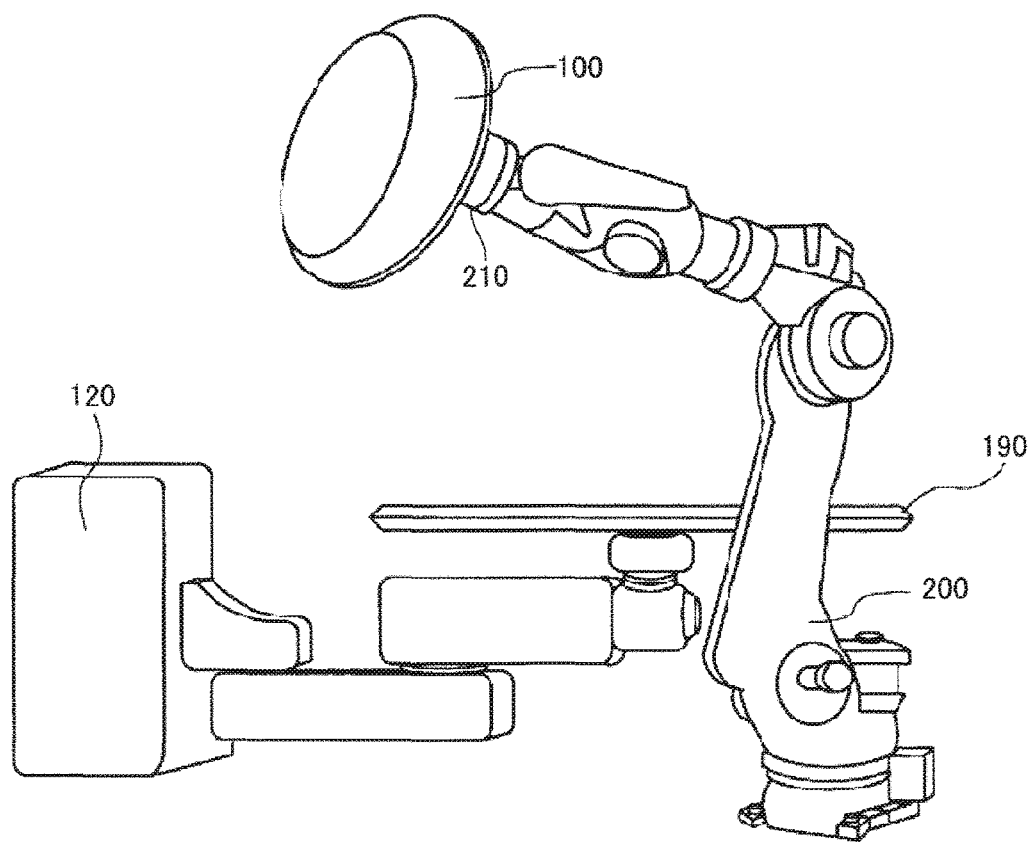
FIG. 1 is a diagram illustrating the appearance of a radiation therapy apparatus according to an embodiment of the present disclosure.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same function, operate in a similar manner, and achieve a similar result.

FIG. 1 is a diagram illustrating the appearance of a radiation therapy apparatus 1 to which a drive control technique according to an embodiment of the present disclosure is applied. The radiation therapy apparatus 1 comprise an X-ray head 100 configured to radiate X-rays, a six-axis manipulator 200 configured to drive the X-ray head 100, and a control device 120 configured to control the operations of the X-ray head 100 and the six-axis manipulator 200. The control device 120 includes an overall control unit and a sub-unit controller, which will be described later. The six-axis manipulator 200 has an arm 210 whose end part is connected to the X-ray head 100, and the arm 210 is capable of moving in directions of three axes as well as rotating around the axes. The entire X-ray head 100 has such a size and weight that it can be mounted to the arm 210. When a patient is subjected to X-ray therapy lying on a couch 190, the six-axis manipulator 200 moves the X-ray head 100 along a predetermined radiation path so as to direct the X-ray head 100 in the desired direction.

The robot-type radiation therapy apparatus 1, which includes the six-axis manipulator 200 mounting the X-ray head 100, can omnidirectionally irradiate an affected area from any point on a virtual spherical surface. The radiation therapy apparatus 1 is configured to focus a dose of X-rays onto the affected area while reducing a dose thereof applied to nearby normal cells, thereby minimizing side effects.

In an embodiment of the present disclosure, the radiation therapy apparatus irradiates the affected area with X-rays, not from an irradiating position (node) as in a conventional apparatus while remaining stationary, but on a path passing through multiple predetermined irradiating positions while moving along a hypothetical spherical surface. Accordingly, the time period for stabilizing vibrations generated in association with acceleration and deceleration is unnecessary, which can reduce treatment time. From the opposite perspective, a greater number of actual nodes (positions and directions of irradiation) are set, which can reduce the dose of X-rays applied to normal cells.

When radiation target is a respiratory or cardiac tumor, such a tumor itself moves in a complex manner, accelerating and decelerating in association with breathing and heartbeat of a patient. In contrast to conventional approaches, instead of causing the entire X-ray head 100 to track the motion of the lungs using the six-axis manipulator 200, an irradiation spot is caused to track the motion of the lungs using a swing collimator that is mounted to the end part of the X-ray head. A configuration and operation of the swing collimator will be described later in detail.

Positional accuracy as in the conventional stationary radiation method is required also when dynamic tracking control is performed in which the movement of a lung tumor is tracked using the swing collimator while the X-ray head 100 is continuously moved along the spherical surface. Specific means is required for achieving higher positional accuracy in dynamic radiation while controlling the six-axis manipulator 200 and a drive device of the swing collimator in the X-ray head 100 in a cooperative manner.

In order to implement this, three solutions are provided as follows.

(1) Drive control using feedforward control
(2) Improvement in mechanical mechanism for swinging movement
(3) Drive control based on mechanical elements The first solution, i.e., utilization of feedforward control, is based on an awareness that, under typical control of position feedback (FB) and speed feedback (FB), position deviation increases in dynamic tracking control. Thus, feedforward (FF) control is added. The FF control includes speed FF control and acceleration FF control with respect to a target speed. Use of speed FF and acceleration FF in addition to position FB and speed FB can reduce position deviation, which is caused by the movement of a tumor with breathing and heartbeat with repeating acceleration and deceleration. In particular, it is possible to reduce the effects of acceleration torque generated by the moment of inertia of components during acceleration.

The second solution, i.e., improvement in mechanical mechanism, is based on an awareness that the mechanical loads to the swing collimator and its drive mechanism may affect dynamic tracking control depending on the posture of the X-ray head. Thus, two improvements in mechanical mechanism are provided.

Firstly, the rotational center of the swing operation of a swing portion, which includes the swing collimator and its accessories, is aligned with the center of gravity of the swing portion. Here, "aligned" does not indicate perfect alignment, but includes a reasonable range. The swing collimator is configured to be moved in three dimensions including up-and-down direction and right-and-left direction by the movement of the six-axis manipulator 200. If the rotational center of the swing portion is deviated from the center of gravity, the effects of such a deviation due to the center of gravity result in an error in mechanical load. Further, the X-ray head 100 mounted to the six-axis manipulator 200 is configured to move at a constant speed on a surface of a sphere having a radius R about the isocenter while the radiation axis is directed toward the isocenter. The deviation of the center of gravity from the rotational center of the swing portion causes variation in centrifugal force, and affects the operation of the six-axis manipulator 200. Therefore, the rotational center of the swinging movement is aligned with the center of gravity of the swing portion, thereby minimizing the effects of variation in load.

Secondly, the moments of inertia about each of the X-axis and Y-axis, which form reference planes passing through the rotational center (pivot of swinging movement) of the swing portion, are substantially equally distributed. The moment of inertia does not create a mechanical load at a constant speed, but emerges as a mechanical load during acceleration or deceleration. The equal distribution of the moment of inertia is effective in enhancing tracking of acceleration and deceleration movements, such as motion of the lungs, which substantially excludes uniform motion.

The third solution, i.e., drive control based on mechanical elements, includes FF control of a mechanical load. This control is based on an awareness that, since mechanical load varies with the posture of the swing collimator (i.e., directions of irradiation of the X-ray head), tracking control is supposed to be more precise by reflecting the variation in mechanical load in feedforward (FF) control. Even when the rotational center of the swing portion is aligned with the center of gravity, variation in mechanical load may occur due to the deviation of the center of gravity caused by irradiating postures, variation with time, friction variation, etc. The load due to deviation of the center of gravity and the variation in load itself are likely to occur when friction is larger. The effects of deviation of the center of gravity can be cancelled such that load FF control is performed in a direction of overcoming friction.

The swing collimator itself may be replaced to change its radiation field into a desired shape, assuming that the moment of inertia is uniformly arranged. In this case, inertia varies with the shapes of the radiation fields. Thus, information on changes in parameters (friction, inertia, etc.) of mechanical elements is held for each swing collimator. Such information is reflected in parameters for load FF control, acceleration FF control, and so on, so as to be able to respond to changes in the radiation field.

Prior to the descriptions of specific configurations of these three solutions, the outline of the radiation therapy to which an embodiment of the present disclosure is applied will be described.

Radiation Therapy Procedure

Figure 2:
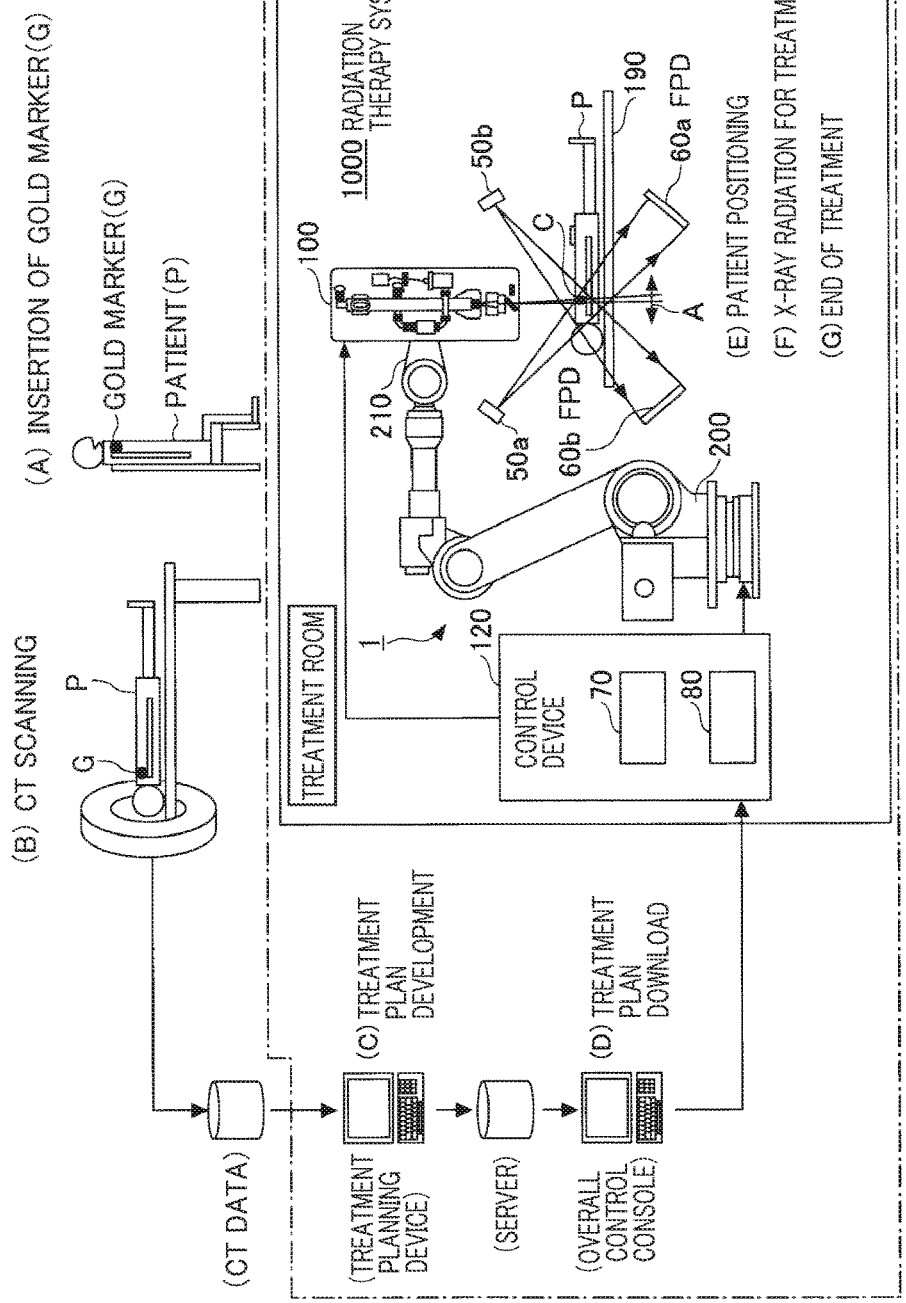
FIG. 2 is a schematic view illustrating a procedure of radiation therapy.

FIG. 2 is a schematic view illustrating the radiation therapy procedure using a radiation therapy system 1000. Following processes (A) to (G) describe the outline of the procedures of the X-ray therapy.

(A) A single or a plurality of markers is implanted near an affected area of a patient P who is subjected to radiation therapy. The marker is made of a material that attenuates radiation, and thus, for example, a gold marker G is used. In the drawing, the single gold marker G is illustrated for the sake of convenience, but a plurality of markers may be used.

The gold marker G is a spherical body having a diameter of about 1.5 mm, and is utilized to specify the affected area in an X-ray image.

(B) After it is confirmed that the gold marker G has been fixed, the patient P is subjected to Computer Tomography (CT) scanning with a CT scanner to obtain CT scan data.

(C) A physician or the like operates a treatment plan device and creates an X-ray treatment plan for the patient P based on the above-described CT scan data. Specifically, a Region of Interest (ROI: image region of interest) in the affected area and target dose distribution are specified. The optimum direction of irradiation, dose, and movement path of the X-ray head 100 are calculated using treatment plan software. In an embodiment of the present disclosure, the movement path of the X-ray head is a continuous path to be followed at a constant speed. The term "X-ray treatment plan" means a plan of direction/dose, etc., for irradiating the affected area of the patient P with X-rays.

(D) An operator downloads the data of the created treatment plan to an overall control console of the radiation therapy apparatus 1.

(E) Lay and position the patient P on the couch.

(F) An operator operates the radiation therapy apparatus 1 so as to irradiate the patient P with X-rays for treatment. X-rays are radiated in such a dose/direction that is optimized in accordance with the treatment plan device. Specifically, the six-axis manipulator 200 drives the X-ray head 100 to move along the specified radiation path to an irradiating position. On the other hand, movement of a body surface near the affected area, heartbeat, and phases of breathing are measured respectively using a body surface monitoring camera 102 (see FIGS. 3 and 4), a heartbeat monitoring device, and a breathing phase monitoring device, to set the initial parameters, etc., for the radiation therapy apparatus 1, and irradiation is performed when the apparatus passes through the irradiating position.

(G) The treatment is finished, and the patient P is set down from the couch and is allowed to exit from the treatment room.

In the above-described process (F), the affected area is not irradiated with X-rays according to the created X-ray treatment plan, since there is the body motion of the patient P when X-rays irradiate the affected area. For example, if the patient P has lung cancer and the affected area is irradiated with X-rays, the affected area is displaced by the breathing of the patient, which makes it difficult to precisely irradiate the affected area with X-rays.

Therefore, in an embodiment of the present disclosure, a second collimator is disposed inside a first collimator that is disposed in the X-ray head 100, and the second collimator are swung in at least one direction or in two directions orthogonal to each other (one dimension or two dimensions). Accordingly, the moving affected area is irradiated with X-rays while being tracked. A description of a specific configuration of a collimator device comprising the first and second collimators is deferred.

Figure 3:
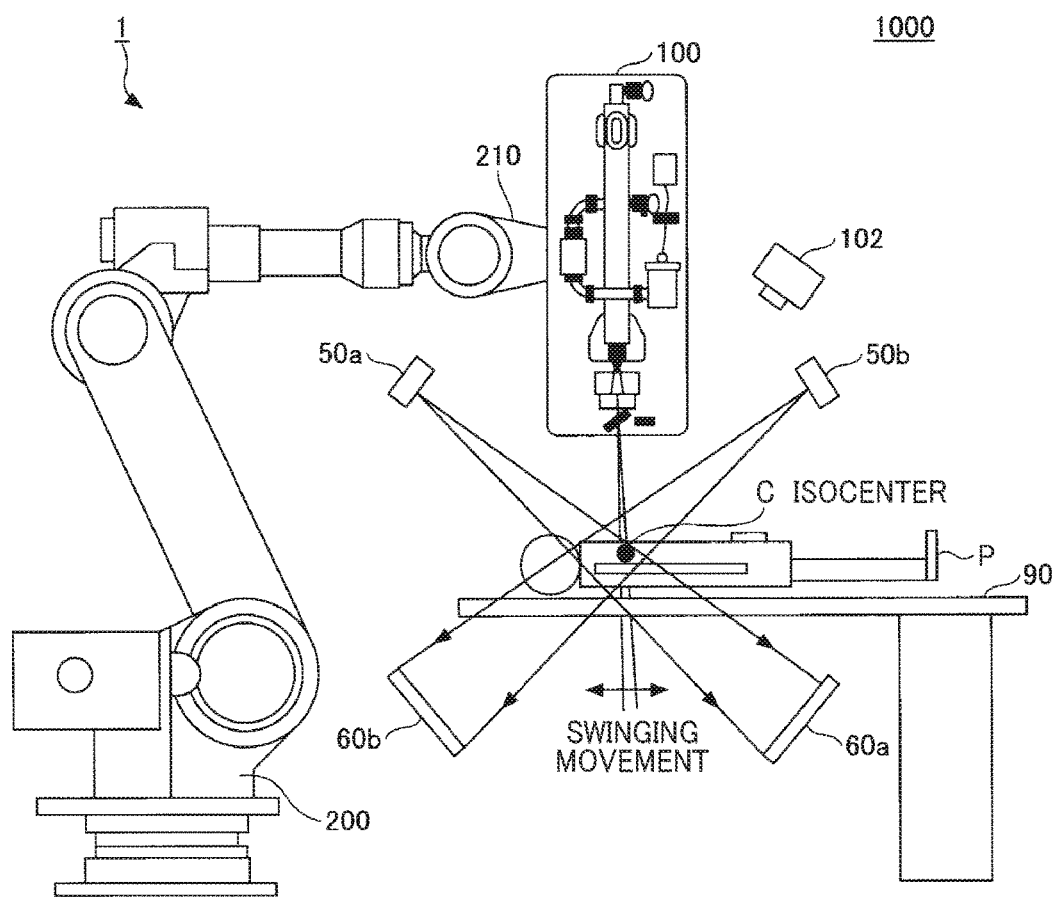
FIG. 3 is a diagram illustrating moving-body tracking.

FIG. 3 is a diagram illustrating dynamic tracking. The six-axis manipulator 200 three-dimensionally moves the X-ray head 100 to an appropriate position as well as directs the X-ray head 100 in an appropriate direction, thereby causing the second collimator to swing in the X-ray head 100. X-rays for detecting a marker position emitted from a pair of X-ray tubes 50*a*, 50*b* are detected by Flat Panel Detectors (FPD) 60*a*, 60*b*, which are flat X-ray detectors. The directions of X-ray radiation from the pair of X-ray tubes 50*a*, 50*b* are set so as to be orthogonal to each other. The shadow of the gold marker G, which attenuates the X-rays, is reflected in the X-ray-detected image obtained by the FPDs 60a, 60b. For example, the center of the shadow is obtained through image processing or the like, and combined with CT image information to calculate the body-motion position information on the affected area, and the swing of the second collimator is controlled based on the calculated body-motion position information such that the radiation field tracks the body motion.

Figure 4:
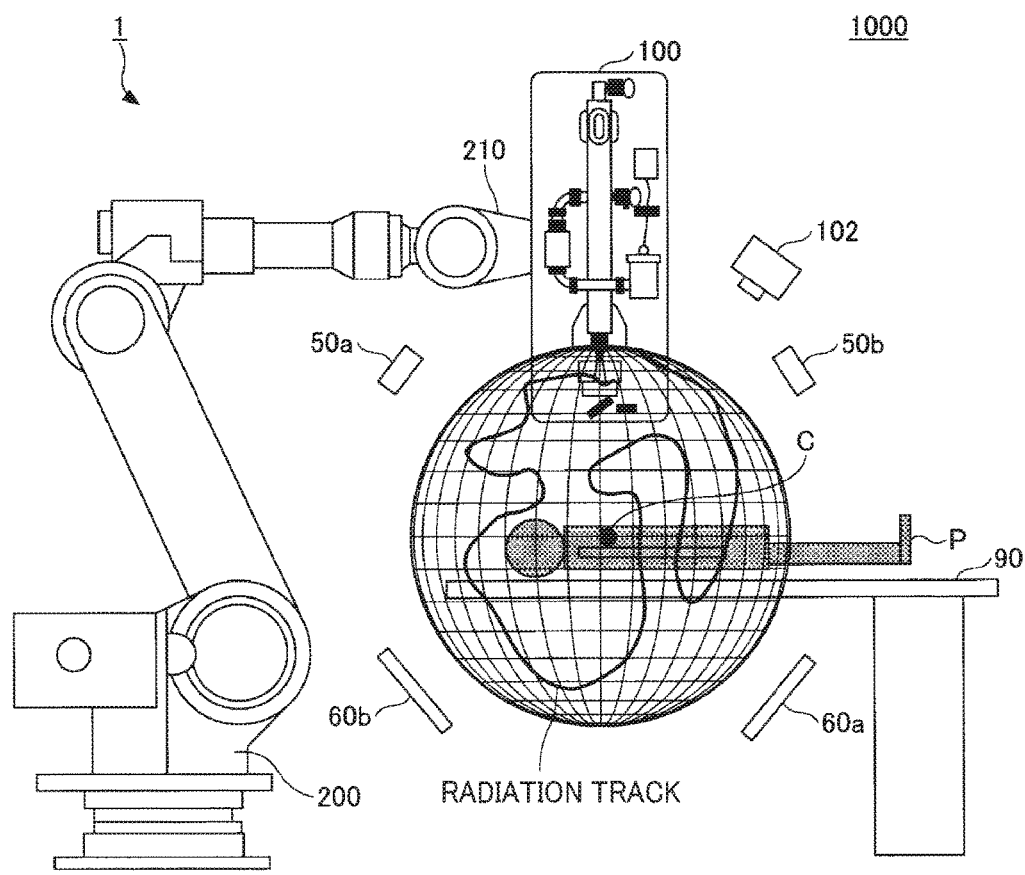
FIG. 4 is a diagram illustrating continuous irradiation in multiple directions with moving-body tracking.

FIG. 4 is a diagram illustrating continuous irradiation in multiple directions with dynamic tracking. The X-ray head 100 mounted to the six-axis manipulator 200 can move freely on a surface of a sphere having a radius R of Source Axis Distance (SAD) such that the X-ray radiation is directed at all times toward an isocenter C, which serves as the origin (irradiated part). In this example, the SAD indicates a distance from an X-ray source to the isocenter C. As the SAD, 600 mm is set for a head, while 800 mm is set for a torso.

The swing collimator mounted to the X-ray head 100 is configured to emit X-rays while being directed to the position of a tumor obtained by calculation. The position of the tumor, i.e., radiation target, is determined such that the position of the gold marker G is detected by a kV-imager device, which includes the X-ray tubes 50a, 50b and the FPDs 60a, 60b, and the position of the tumor is calculated based on the CT information obtained by scanning beforehand.

Assuming that the X-ray head 100 has a weight of about 200 kg, it is difficult to make the X-ray head 100 itself track the motion of the lungs using the six-axis manipulator 200, in view of a typical breathing period (about 0.5 Hz) and heartbeat (about 1 Hz). This is because the six-axis manipulator 200 has a resonance frequency of about 4 Hz, and a crossover frequency (about 2 Hz) for control cannot be raised. With this crossover frequency, sufficient positional accuracy cannot be acquired.

In contrast, in an embodiment of the present disclosure, the six-axis manipulator 200 is operated so that the X-ray head 100 moves at a constant speed along the surface of a virtual sphere at all times, and only the swing portion of the swing collimator which has a small mass moves in accordance with the motion of the lungs and the heart. Accordingly, it is possible to have a great crossover frequency, thereby considerably improving position tracking accuracy.

Configuration of the X-Ray Head 100

Figure 5:
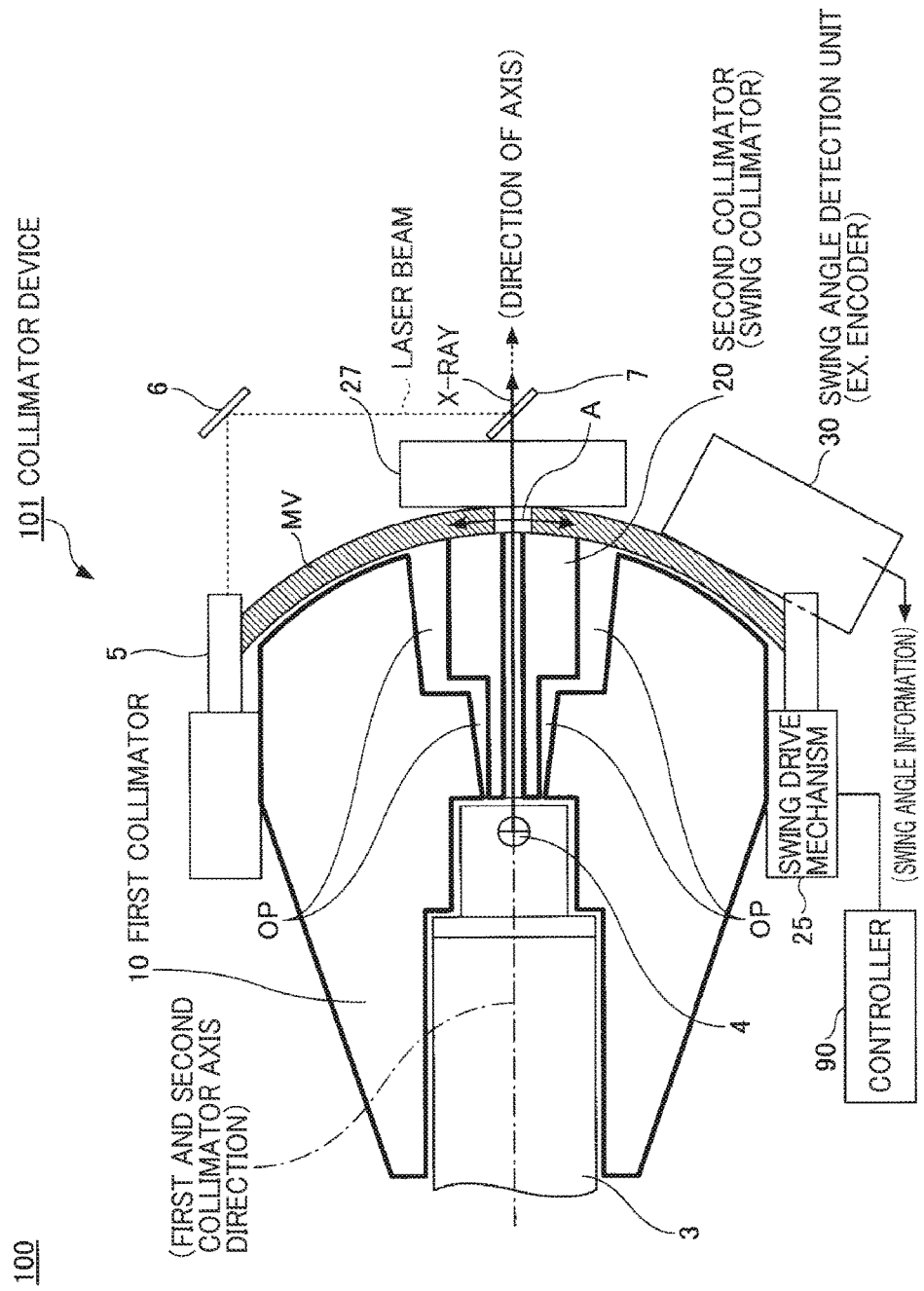
FIG. 5 is a schematic view illustrating a principal part of an X-ray head.

FIG. 5 is a schematic view illustrating a principal part of the X-ray head 100. The X-ray head 100 functions as a radiation emitting apparatus, and comprises a collimator device 101 as its principal part. The collimator device 101 comprises a target 4 for generating X-rays, the first collimator 10, the second collimator 20, and a swing drive mechanism 25 configured to swing the second collimator 20 within the first collimator 10. An actual radiation field is formed by the first collimator 10, the second collimator 20, and the swing drive mechanism 25 operating together.

The first collimator 10 has a center axis in a direction indicated by a dot-and-dash line, and has a shape that is symmetrical about the center axis. The center axes of an acceleration tube 3 and the target 4 are aligned with the axis of the first collimator 10 such that the axis direction of the first collimator 10 is aligned with the traveling direction of accelerating electron beams.

The second collimator 20 is disposed, with a gap (OP), within the first collimator, and allows the X-rays generated in the target 4 to pass therethrough in the axis direction of itself. In the drawing, a line of an arrow illustrated with a thick line in the lateral direction from the target 4 indicates the direction of the X-ray radiation. The first collimator 10, the second collimator 20, and the target 4 are made of, for example, tungsten (W). A dosimeter for measuring a dose of X-rays, e.g., an ion chamber 27, is provided on the emitting side of the second collimator 20. The direction of the X-ray radiation, that is, the direction of irradiation, can be also measured with reference to dose distribution, etc., in the ion chamber 27.

A laser targeting unit 5 is provided, which is configured to emit visible laser light (e.g., red light) onto a surface of a suitable member coupled to the first collimator 10. The optical axis of the visible laser light emitted from the laser targeting unit 5 is aligned with the X-ray axis along the traveling direction of the X-rays using an optical system such as mirrors 6 and 7. The X-ray-incident position can be found by observing the body surface of the patient painted with the visible laser light.

The swing drive mechanism 25 is configured to move a movable member MV based on a control signal from a controller 90 installed in the X-ray head 100, so that the second collimator 20 connected to the movable member MV is rotated (swung) in the two directions indicated by arrow A.

The target 4 is positioned on the axis of the second collimator 20. For example, bearings are provided between the spherical surface of the first collimator, which is a surface of the sphere whose center is the target 4, and the movable member MV coupled to the second collimator 20. The bearings are coupling members (linear slides) comprising arc-shaped curvilinear-motion bearings in two directions so as to allow movements of two-degree-of-freedom, for example. The insertion of the bearings supports the movable member MV as well as enables the smooth swinging movement of the second collimator 20 while the target 4 serves as the rotational center. A portion relating to the swinging movement, which includes the second collimator, the bearings, and the movable member MV, is referred to as the "swing portion". The swing drive mechanism 25 is configured to swing the swing portion to the desired position, so that the affected area can be precisely irradiated.

The sliding directions of the bearings and the drive axes of the second collimator 20 are aligned, so that smooth drive can be implemented. The movement in the X-axis direction involves the bearings in one axis direction, while the movement in the Y-axis direction involves the bearings in the other axis direction. The drive means also drives the swing portion in a corresponding one of the axes directions that also corresponding to that of a drive means. When drive is performed in a direction intermediate between the X-direction and the Y-direction, the bearings cooperate with the drive means along two axes to achieve smooth movement without vibrations.

A swing angle detection unit 30 is provided as an example of a deviation detection means. The swing angle detection unit 30 is configured to detect swing displacement (swing angle) relative to the reference point of the second collimator 20 to output its result as swing angle information (or displacement information). The swing angle detection unit 30 may be an optical angle measurement device of an autocollimator type which uses a semiconductor laser and optical system, or an angle detector of an encoder type which uses an encoder sensor.

Electron beams emitted from an electron gun 2 (see FIGS. 6 and 7), installed in the X-ray head 100, are accelerated through the acceleration tube 3 to collide with the target 4, so that the electron beams are converted into X-rays. The radiation area of X-rays generated by the target 4 is narrowed by the second collimator 20, to form a predetermined radiation field for an affected area. The first collimator 10 restrains the X-rays generated by the target 4 from leaking to the exterior.

The controller 90 is configured to perform drive control of the swing drive mechanism 25 to move the movable member MV in the direction indicated by the arrow A (up and down direction in the drawing), so that the second collimator 20 swings in the direction of the arrow A. The swing displacement (swing angle), which is a swing amount relative to the reference point, is detected by the swing angle detection unit 30. The detected swing displacement is used, for example, for feedback control and feedforward control, to control the swinging movement, so that the movement is stabilized. The movable member MV is capable of swinging not only in the direction of the arrow A (one-dimensional operation), but also the direction vertical to the paper on which the figure is drawn (front and back direction). Accordingly, the second collimator 20 is capable of swinging in the front and back direction of the paper, and thus the second collimator 20 is configured to swing in two directions (two dimensionally) of the up and down direction and the vertical direction of the paper. Such two-dimensional swing drive may be performed using the swing drive mechanisms 25 individually provided for the directions. Further, detection/output of swing displacement can be performed by the single swing angle detection unit 30, or the swing angle detection units 30 individually provided for the directions. The swing drive mechanism 25 is configured, for example, with a voice coil motor, thereby enabling swinging movement with higher speed and precision.

The X-ray head 100 further includes the electron gun 2 and the controller 90 (see FIG. 7), which will be described later, in addition to the acceleration tube 3, the target 4, the laser targeting unit 5, the first collimator 10, the second collimator 20, the swing drive mechanism 25, and the swing angle detection unit 30 in FIG. 5.

(X-Ray Generation Unit)

Figure 6:
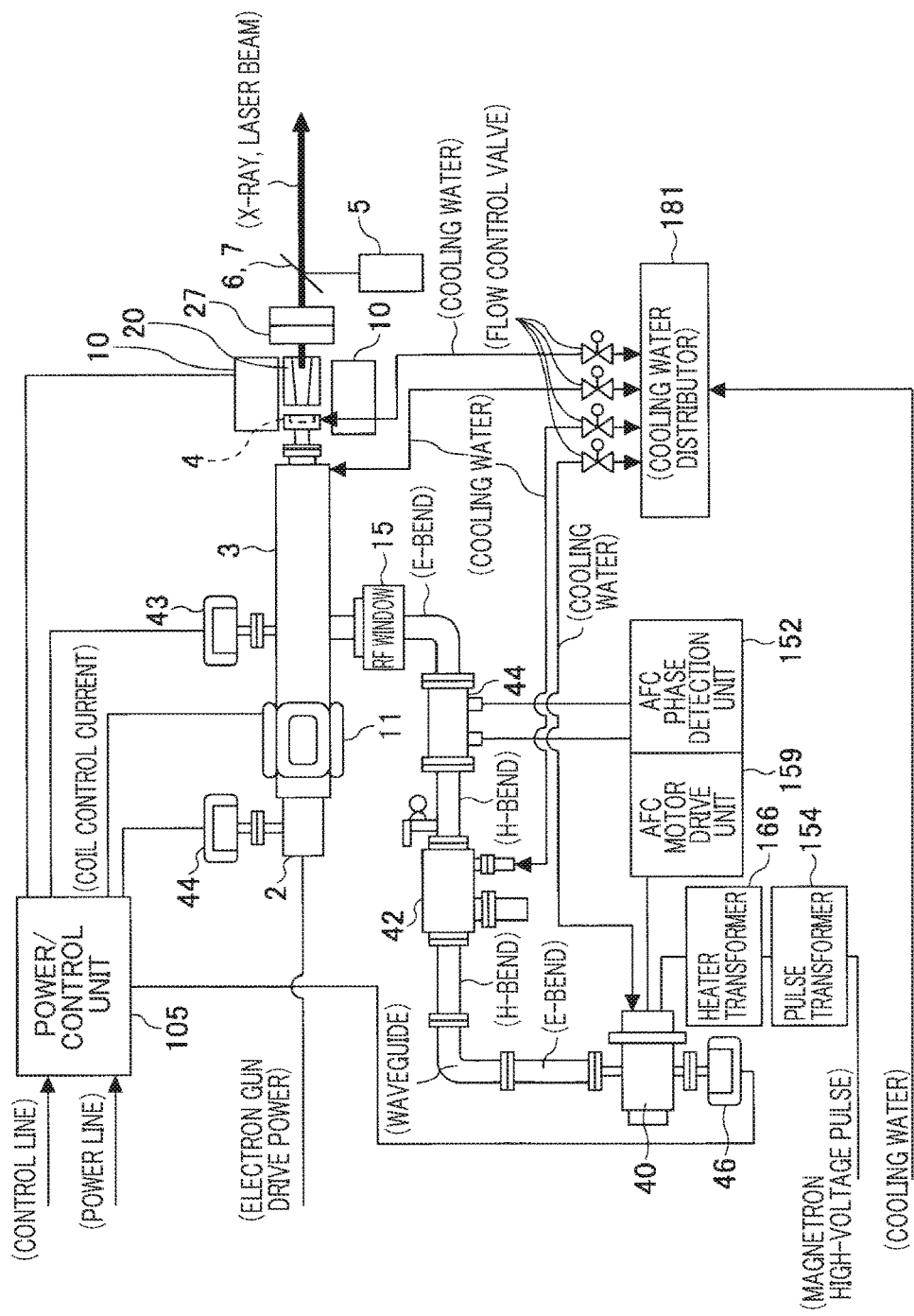
FIG. 6 is a schematic view illustrating a portion related to generation of X-rays and generation and acceleration of electron beams in the X-ray head.

FIG. 6 is a schematic view illustrating a portion particularly relating to the generation of X-rays and the generation and acceleration of electron beams in the X-ray head. A power/control unit 105 is configured to supply power or supply a control signal to a predetermined place. Electron-gun drive power is supplied from the power/control unit 105 to the electron gun 2, and the interior of the electron gun 2 is a vacuum atmosphere created by driving an ion pump 43. The acceleration tube 3 is configured to accelerate electron beams emitted by the electron gun 2 in the interior of the tube. The interior of the acceleration tube 3 is maintained in a vacuum atmosphere by operating another ion pump 43. A steering coil 11 is configured to apply a magnetic field for making fine adjustments to the direction of acceleration in the electron beams. The target 4 is mounted near the end part of the acceleration tube 3 (right-side in the drawing). When the electron beams collide with the target 4, X-rays are generated. Thus, the target 4 is an electron-beam-to-X-ray conversion unit. The X-rays generated as such are shaped into a predetermined radiation field in the second collimator 20 that is configured to swing. As described with reference to FIG. 5, the visible laser light outputted from the laser targeting unit 5 is guided by the mirrors 6 and 7, so that the optical axis of the X-rays is aligned with the optical axis of the laser beams (center axis of laser beams).

Coolant from a coolant distributor 181 is controlled by a flow control valve as to its supply amount, and supplied to predetermined places. In particular, the coolant at a constant temperature is supplied to the target 4, the acceleration tube 3, a magnetron 40, a circulator 42, and the like. When a magnetron high-voltage pulse is supplied to a pulse transformer 154, the high voltage of the pulse transformer 154 is applied via a heater transformer 166 to the magnetron 40, and the magnetron 40 generates and outputs a high-frequency electromagnetic wave. The ion pump 46 is operated to create a vacuum atmosphere near the magnetron 40. The electromagnetic wave generated and outputted by the magnetron 40 is introduced, through waveguide devices such as an E-bend, a flexible waveguide, an H-bend, a circulator 42, an H-bend, and a coupler 44, and further via an RF window 15, to the acceleration tube 3. The Automatic Frequency Control (AFC) phase detection unit 152 is configured to detect a phase difference between a traveling wave and a reflected wave that are guided in the waveguide devices utilizing two terminals of the coupler 44. An AFC motor drive unit 159 connected to the cavity of the magnetron 40 is configured to control the size of the cavity according to the detected phase difference, thereby changing and controlling oscillation frequency. As a result, Automatic Frequency Control (AFC) is performed, that is, a frequency shift of a high-frequency electromagnetic field is fed back so as to stably control the frequency.

When the high-frequency electromagnetic wave is introduced from the RF window 15 into the acceleration tube 3, an electric field suitable for acceleration is generated along the center axis of the tube, to accelerate the electron beams. In other words, the electron beams emitted from the electron gun 2 are accelerated by virtue of the high-frequency electromagnetic field that is generated with introduction of the electromagnetic wave into the acceleration tube 3, and resultant beams collide with the target 4 so that the X-rays are generated. With such a configuration that the electron beams emitted toward the target 4 have a spot diameter of, e.g., 1 mm or less and the target 4 has an X-ray guide aperture having a diameter of 0.6 mm or less, it is possible to generate X-rays having higher energy and a smaller beam spot diameter.

Collimator Drive Control System

Figure 7:
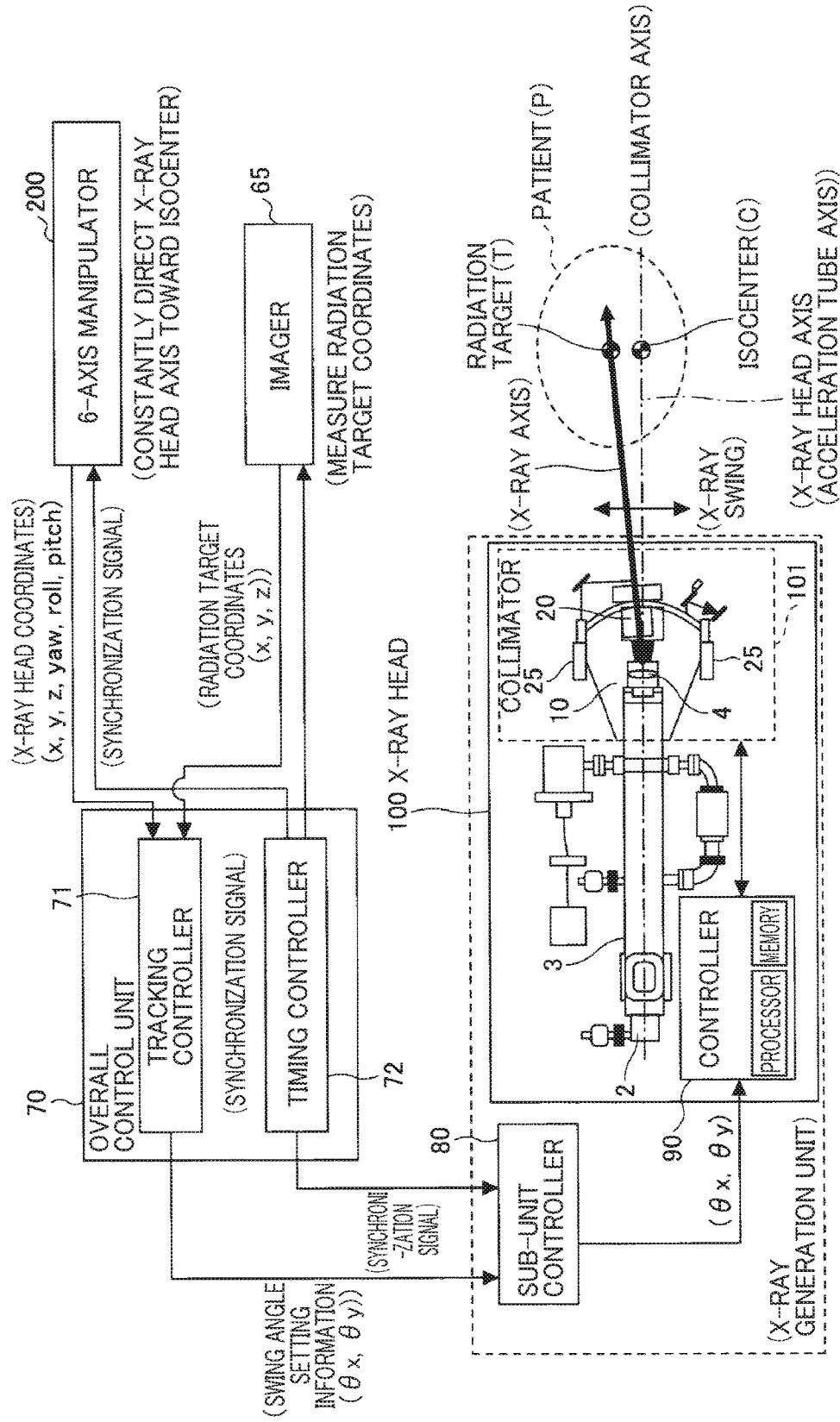
FIG. 7 is a diagram illustrating the outline of a control system configured to perform drive control of a collimator device.

FIG. 7 is a diagram illustrates the outline of a control system configured to perform drive control of the collimator device 101. The collimator device 101 is controlled using an overall control unit 70, a sub-unit controller 80, and the controller 90 in the X-ray head 100. The overall control unit 70 may be included in, for example, the control device 120 in FIG. 1. The sub-unit controller 80 may be included in the control device 120 or in the X-ray head 100. Alternatively, the sub-unit controller 80 may be disposed, as a microchip, outside the X-ray head 100.

The overall control unit 70 comprises a tracking controller 71 and a timing controller 72. The timing controller 72 is configured to generate synchronization signals for synchronizing the devices in the radiation therapy apparatus 1, and supply the synchronization signals to the six-axis manipulator 200, an imager 65, the sub-unit controller 80, and the like. The imager 65 includes a set of the X-ray tube 50a and the FPD 60a and another set of the X-ray tube 50b and the FPD 60b, described above, and is a device directed to capture of X-ray images in the vicinity of a tumor.

The tracking controller 71 is configured to receive the coordinates (x, y, z, yaw, roll, pitch) of the X-ray head 100 from the six-axis manipulator 200. The six-axis manipulator 200 drives the X-ray head 100 so as to direct the X-ray head 100 toward the isocenter at all times. As a coordinate system, the isocenter C is set as the origin, the x-axis and the y-axis are set in two directions on a plane, and the z-axis is set in a direction vertical to the xy plane. The "yaw" is the amount of rotation about the Z-axis, the "roll" is the amount of rotation about the x-axis, and the "pitch" is the amount of rotation about the y-axis.

The tracking controller 71 is configured to receive also the coordinates (x, y, z) of the radiation target from the imager 65, and calculate swing angles θx and θy at which the second collimator 20 should be positioned, based on the coordinates (x, y, z) of the radiation target and the current coordinates (x, y, z, yaw, roll, pitch) of the X-ray head 100. The obtained swing angles are supplied to the sub-unit controller 80 as swing angle setting information (θx, θy).

The sub-unit controller 80 is configured to receive the swing angle setting information (θx, θy) from the tracking controller 71, and supply the swing angle setting information (θx, θy) to the controller 90 installed in the X-ray head 100. Such swing angle setting may be directly inputted from the tracking controller 71 to the controller 90 in the X-ray head 100.

The controller 90 in the X-ray head 100 is configured to receive the swing angle setting information, perform arithmetic processing for feedback and feedforward control, and output such control information to the swing drive mechanism 25 (see FIG. 5) of the collimator device 101. The controller 90 may be a control IC including a processor and memory. The swing drive mechanism 25 is configured to swing the swing portion including the second collimator based on the received control information, so that a swing angle results in the swing angle specified by the swing angle setting information (θx, θy).

By repeating the above described operations, the X-ray axis is directed toward the radiation target at all times, and even when a body is in motion, the affected area is appropriately irradiated with X-rays. As illustrated in the lower right side of FIG. 7, even if a radiation target T of the patient P deviates from the collimator axis serving as the reference axis of radiation, the X-ray axis tracks the target (see a thick arrow) with the swinging movement (see two-headed arrow) of the collimator. Such a sequence of operations is implemented on a real-time basis in accordance with the synchronization signals that are generated and outputted by the timing controller 72 in the overall control unit 70, thereby being able to perform dynamic tracking at a higher speed.

First Embodiment

In a first embodiment, drive control of the collimator device 101 using the first solution, i.e., feedforward control, is provided.

Figure 8:
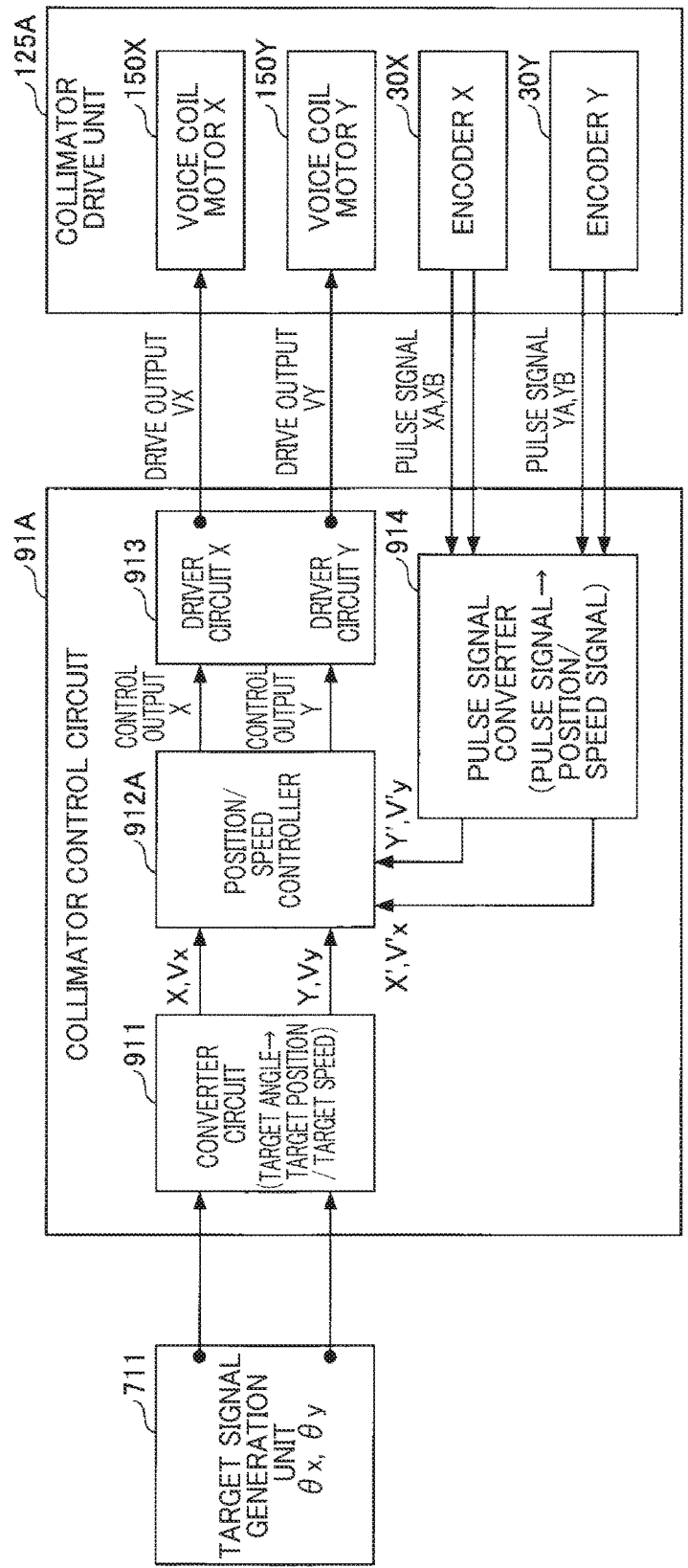
FIG. 8 is a block diagram illustrating a control system configured to perform drive control of a collimator device.

FIG. 8 is a block diagram illustrating a drive control system according to the first embodiment. The drive control system in FIG. 8 includes a target signal generation unit 711, a collimator control circuit 91A, and a collimator drive unit 125A. The target signal generation unit 711 is implemented by the action of the tracking controller 71. The collimator control circuit 91A is included in the controller 90 in the X-ray head 100. The collimator drive unit 125A includes the swing drive mechanism 25 and the swing angle detection unit 30 of FIG. 5. In this example, voice coil motors 150X, 150Y are used as the swing drive mechanism 25, while encoders 30X, 30Y are used as the swing angle detection unit 30.

The collimator control circuit 91A comprises a converter circuit 911, a position/speed controller 912A, a driver circuit 913, and a pulse signal converter 914. Target signals θx, θy, indicative of the swing angle of the target, are inputted from the target signal generation unit 711 via the sub-unit controller 80 (see FIG. 7) to the converter circuit 911. The converter circuit 911 is configured to convert the inputted angle information into target position (X, Y) and target speed (Vx, Vy), and supply such conversion results to the position/speed controller 912A.

On the other hand, pulse signals XA, XB and YA, YB indicative of current angle information on the second collimator 20 are inputted from the encoders 30X, 30Y in the collimator drive unit 125A to the pulse signal converter 914. A pair of pulse signals XA, XB indicates a phase difference about the X-axis, while a pair of pulse signals YA, YB indicates a phase difference about the Y-axis. The pulse signal converter 914 is configured to transform the inputted pulse signals XA, XB and YA, YB into a detection position (X', Y') and a detection speed (V'x, V'y), and supply such transformation results to the position/speed controller 912A.

The position/speed controller 912A is configured to generate control signals X, Y for the position and speed of the second collimator 20 to track the moving body, based on the target position (X, Y), the target speed (Vx, Vy), the detection position (X', Y'), and the detection speed (V'x, V'y), and output the signals to the driver circuit 913. The driver circuit 913 includes a driver circuit X configured to perform drive control of the voice coil motor 150X, and a driver circuit Y configured to perform drive control of the voice coil motor 150Y. The driver circuit X is configured to output a drive signal VX to a voice coil motor X. The driver circuit Y is configured to output a drive signal VY to a voice coil motor Y.

Figure 9:
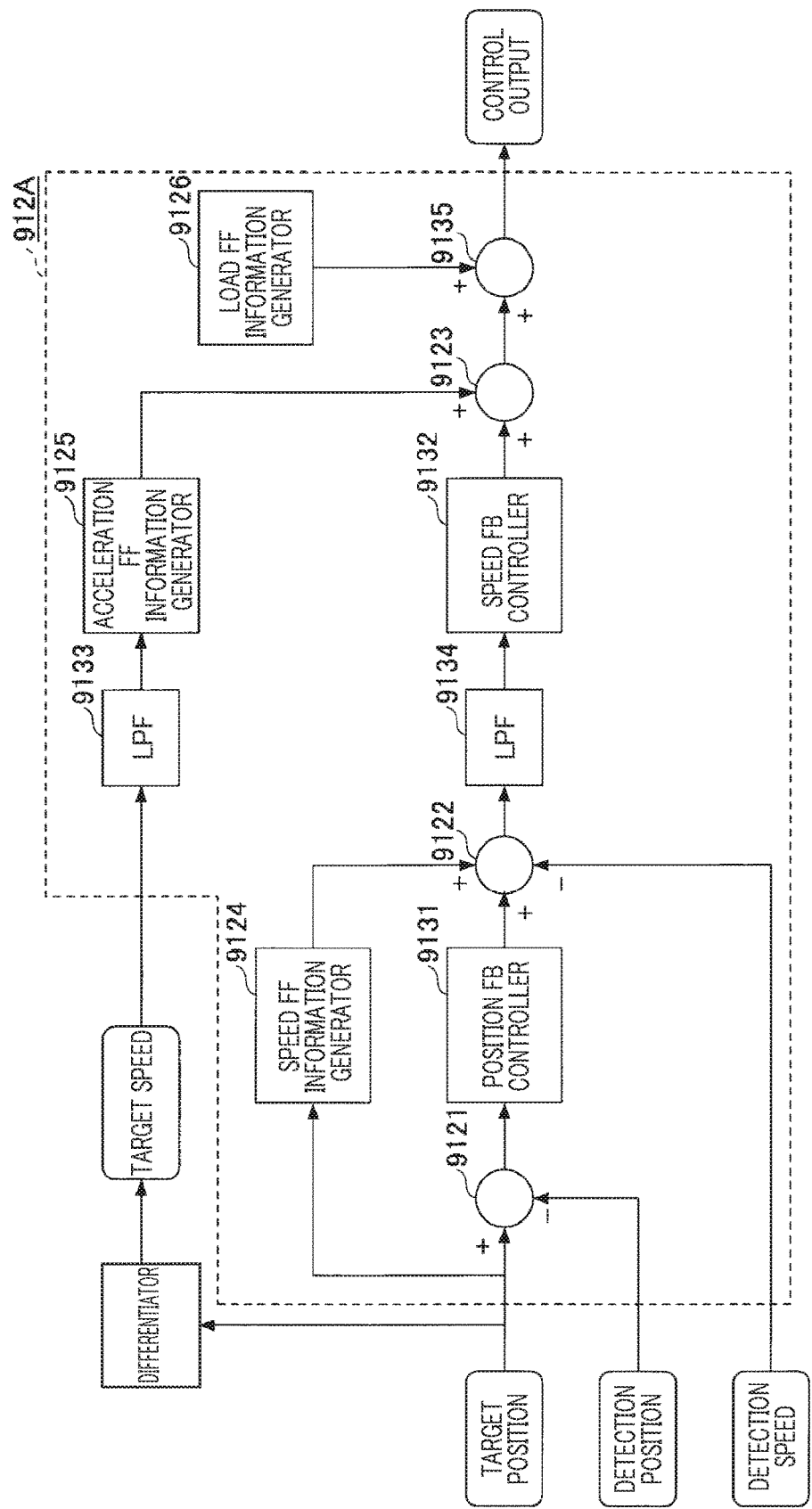
FIG. 9 illustrates generation of control outputs for performing drive control of a head movable collimator.

FIG. 9 illustrates generation of control outputs implemented in the position/speed controller 912A. The configuration and operation in FIG. 9 correspond to the first solution in that dynamic tracking radiation is implemented while an irradiation head (e.g., the X-ray head 100) is continuously moved, and includes generation and utilization of feedforward information.

It is difficult to deliver high-precision tracking performance using only feedback control, with respect to a target, such as a lung tumor, which moves in a complex manner involving both acceleration and deceleration. In order to solve such a problem, the position/speed controller 912A implements feedforward control with excellent tracking performance.

An X-ray radiation target position and a target speed obtained by differentiation and inputted from the converter circuit 911. Further, the detection position and the detection speed indicative of the actual irradiation position and speed are inputted from the pulse signal converter 914.

The position/speed controller 912A comprises a first arithmetic circuit 9121, a second arithmetic circuit 9122, a third arithmetic circuit 9123, a fourth arithmetic circuit 9135, a speed FF information generator 9124, an acceleration FF information generator 9125, a load FF information generator 9126, a position FB controller 9131, a speed FB controller 9132, and low-pass filters 9133, 9134.

The first arithmetic circuit 9121 is configured to calculate a difference between the target position and the detection position, and output such arithmetic result to the position FB controller 9131. The position FB controller 9131 is configured to generate position feedback (FB) information based on the difference.

The speed FF information generator 9124 is configured to differentiate the target position to generate speed FF information.

The second arithmetic circuit 9122 is configured to perform an arithmetic operation based on three pieces of information, which are position FB information outputted from the position FB controller 9131, speed FF information outputted from the speed FF information generator 9124, and the detection speed. More specifically, a difference between the speed FF information and the detection speed is obtained, and this difference and the position FB information are added together. The operation result is subjected to noise filtration and waveform shaping in the LPF 9134, and inputted to the speed FB controller 9132. The speed FB controller 9132 is configured to output speed FB information.

The acceleration FF information generator 9125 is configured to generate the acceleration FF information based on the target speed. The target speed is calculated by differentiating the target position, and a differential signal is subjected to noise filtration and waveform shaping in the LPF 9133, and then is inputted to the acceleration FF information generator 9125. The acceleration FF information is used for performing control so as to cancel acceleration torque generated by the moment of inertia (inertia) of mechanical parts during acceleration.

The third arithmetic circuit 9123 is configured to add the speed FB information outputted from the speed FB controller 9132 and the acceleration FF information outputted from the acceleration FF information generator 9125. The fourth arithmetic circuit 9135 is configured to generate a control signal based on an addition result outputted from the third arithmetic circuit 9123 and load FF information generated in the load FF information generator 9126, and output a control signal. FF load FF information included in the control signal serves to cancel an expected mechanical load. Change in inertia can be restrained by the acceleration FF information contained in the control signal, and change in mechanical load can be handled with the load FF information.

An acceleration FF gain is defined by a reciprocal of a control target model including mechanical inertia. The speed FF is a differential gain. Proportional (P) control may be used for the position FB, while all or a part of Proportional-Integral-Differential (PID) control may be used for the speed FB, or a lead-lag filter may be used therefor.

Control in FIG. 9 may be performed through implementation of an algorithm, or may be performed using a digital circuit or an analog circuit integrated in an IC chip.

With this configuration, collimator drive control can be implemented with higher accuracy with less position error during tracking. In particular, since irradiation is intended to track the motion of an affected area with acceleration/deceleration while the X-ray head 100 is continuously moved, acceleration FF control information is useful in cancelling any change in inertia. Assuming that a breathing period is about 0.5 Hz, a heartbeat period is about 1 Hz, the six-axis manipulator 200 has a resonance frequency of about 4 Hz, and the collimator device 101 has a mechanical resonance frequency of, for example, 90 Hz or more, excellent tracking performance can be implemented by setting a position-control crossover frequency (control bandwidth) to 10 Hz and a speed control crossover frequency to 30 Hz. Further, change in the load generated in mechanical parts can be cancelled using load FF information.

Second Embodiment

A second embodiment provides a second solution, i.e., improvement in mechanical mechanism.

Figure 10:
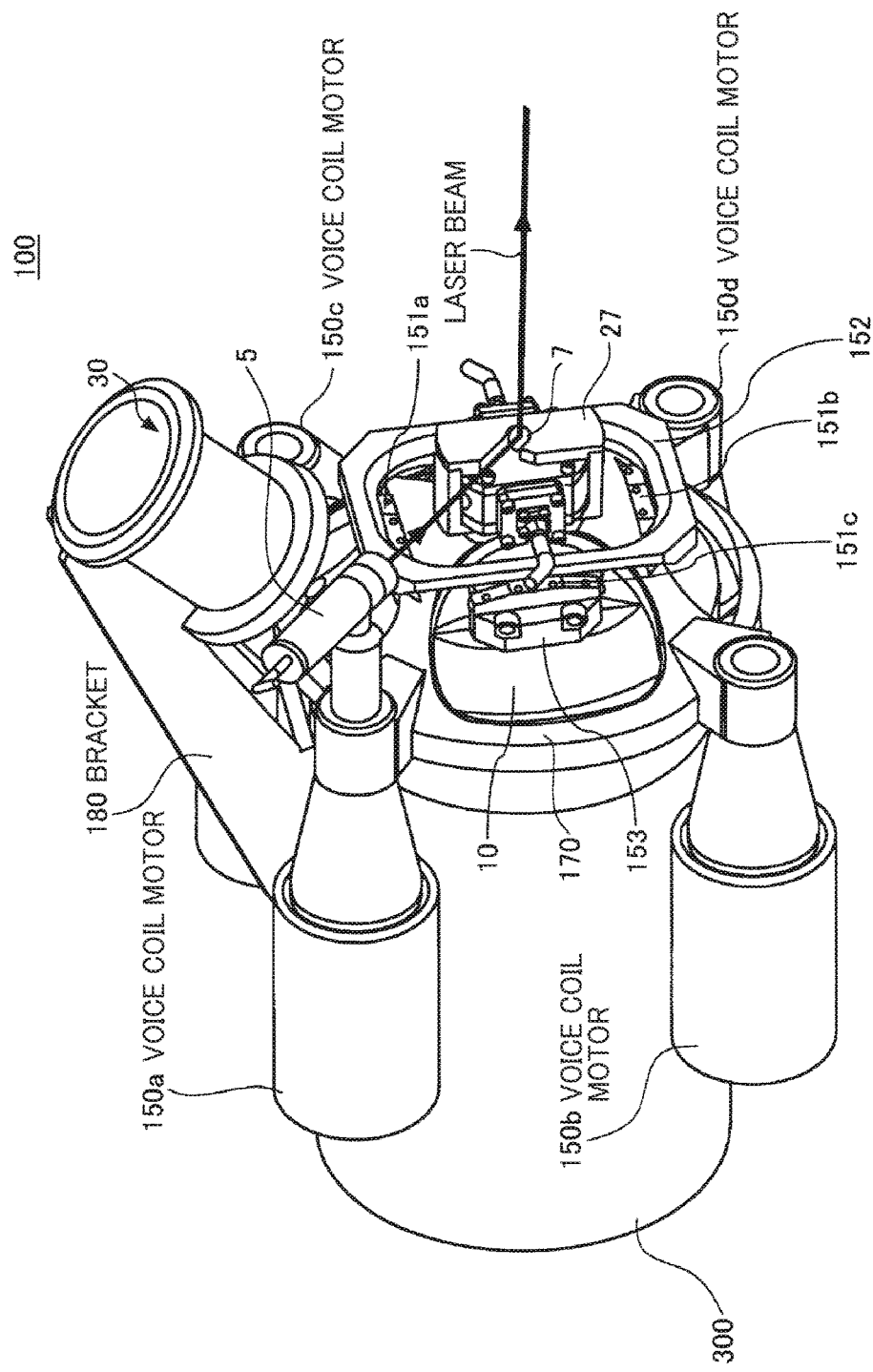
FIG. 10 is a perspective view illustrating an X-ray radiation device.

FIG. 10 is a perspective view illustrating an X-ray radiation device implemented by the X-ray head 100. The X-ray head 100, i.e., the X-ray radiation device, is housed in an X-ray head base 300 serving as housing. The X-ray head base 300 has a hollow cylindrical shape, and houses the first collimator 10 in such a manner as to close an opening of its cylindrical body on one end side (X-ray emitting side). The target 4, which converts the electron beams emitted from the electron gun 2 (see FIG. 7) into X-rays, is provided on the axis of the first collimator 10, and the X-ray axis serving as the reference is aligned with the axis of the first collimator.

Four voice coil motors 150a, 150b, 150c, 150d are provided on an outer peripheral surface of the X-ray head base 300, and are configured to drive the swing portion including the second collimator 20 to swing at least in two directions orthogonal to each other. The voice coil motors 150a, 150b, 150c, 150d are each disposed every quarter of the way around a circumference of the cylindrical body (i.e., at intervals of 90 degrees). The swing angle detection unit 30 is fixed and connected to the end part of a bracket 180 extending from the outer peripheral surface of the X-ray head base 300. In this example, the swing angle detection unit 30 is an autocollimator using a semiconductor laser and an optical system, and a reflective mirror is fixed to the outer surface of a swing base 170 (corresponding to the movable member MV in FIG. 5) opposed to the swing angle detection unit 30. The reflective mirror is not illustrated in the perspective view of FIG. 10.

The end part (X-ray emitting side) of the voice coil motor 150a is provided with the laser targeting unit 5 via an appropriate member. The optical axis of the visible laser light emitted from the laser targeting unit 5 is aligned with the X-ray axis using the optical system configured with a mirror 7, etc. The irradiation target of the X-rays can be confirmed by visually checking the visible laser light. The ion chamber 27 is fixed, using an appropriate member, on the outer surface side of the swing base 170 between the mirror 7 and the second collimator 20, and is capable of easily measuring a radiation dose, the direction of irradiation, etc.

Arc-shaped curvilinear-motion bearings 151a and 151b are disposed between an intermediate member 152 and the swing base 170 coupled to the second collimator 20. Further, arc-shaped curvilinear-motion bearings 151c and 151d that are directed in a direction orthogonal to the direction of the curvilinear-motion bearings 151a, 151b are disposed between the intermediate member 152 and a mounting base 153 on the first collimator 10 (the curvilinear-motion bearing 151d is not illustrated in FIG. 10). With this configuration, the swing base 170 makes smooth swinging movements.

As a feature of this embodiment, the rotational center of the swing portion including components, such as the second collimator 20, the swing base 170, and the curvilinear-motion bearings 151a to 151d, is substantially aligned with the center of gravity of the swing portion. The rotational center of the swing portion is positioned at the target 4 that generates X-rays. Deviation in the center of gravity of the swing portion causes application of loads varying with the directions of swing, whereas, by aligning the rotational center of the swing portion with the center of gravity, such gravity loads with respect to a coefficient of friction between a fixed portion and a movable portion can be brought close to zero. Accordingly, even if the posture of the X-ray head 100 changes with irradiation in multiple directions, change in mechanical load, such as variation in friction force affected by gravity, can be minimized.

Figure 11:
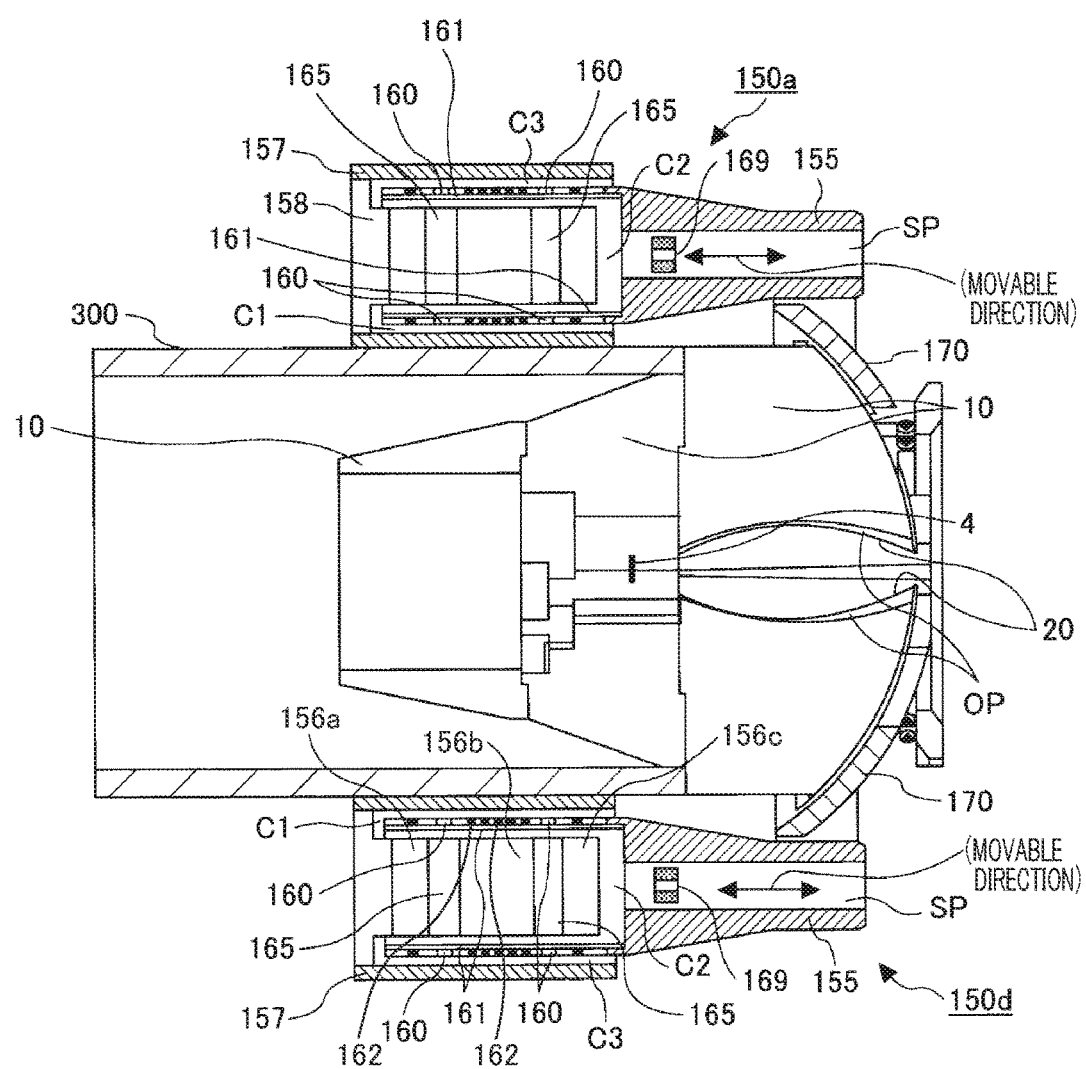
FIG. 11 is a cross-sectional view taken along an axis of a first collimator 10 of FIG. 10.

FIG. 11 is a cross-sectional view taken along the axis of the first collimator 10 of FIG. 10. The first collimator 10 and the second collimator 20 are different in shape from those illustrated in the schematic view of FIG. 5, but the functions and configurations thereof are the same. The second collimator 20 can be in various shapes depending on shapes of its intended radiation fields. The second collimator and the swing portion including it are driven by the voice coil motors 150. In the cross-section of FIG. 11, although only two voice coil motors 150a, 150d are illustrated, four voice coil motors 150a to 150d having the same structure may be used. The electron gun 2, the acceleration tube 3 and the like are omitted for simplicity.

A coil support 155 is the distal end of the voice coil motor 150, has a hollow portion (SP) in the interior thereof, and extends in the direction of X-ray emission. A coil is formed such that a bobbin 161 is connected to the base of the coil support 155 and a conductive wire 162 is wound around the bobbin 161. Two annular coil spacers 160 are disposed, at appropriate intervals, on the outer circumferential side of the bobbin 161. Three coils are formed such that the conductive wire 162 is wound between the two spacers 160 and at locations on the outer side (on the right and left sides in the drawing) in the axis direction of the spacers 160. The two coils on the outer sides and the coil therebetween are wound in opposed directions.

The magnetic circuit of the voice coil motor 150 is fixed to the exterior of the X-ray head base 300. Two cylindrical magnets 165 for forming a magnetic field are provided in the interior of the bobbin 161 as this magnetic circuit. Cylindrical internal yokes 156a to 156c are formed at a location between the two magnets 165 and at locations on the outer sides (on the right and left sides in the drawing) in the axis direction of the magnets 165, while a cylindrical external yoke 157 is formed on the external side of the bobbin 161. The magnetic poles of the magnets 165 exist in the direction of the contacted internal yokes, and the magnetic poles at which the two magnets 165 are opposed are the same pole (when one pole is S, the other is also S). With this configuration, a magnetic flux passes through a cavity between the internal yoke 156 and the external yoke 157, and the magnetic flux and the coils in the cavity are interlinked to pass a current through the coils, so that a mechanical force is generated. The external yoke 157 is coupled to the internal yoke 156a with a base member 158 of a non-magnetic material, which is a bottom portion of the voice coil motor. Note that C1, C2, and C3 in FIG. 11 indicate spaces in the voice coil motor 150.

The swing base 170, whose shape seen from the front is similar to the shape of a steering wheel of an automobile, is disposed at the end of the first collimator 10 and the second collimator 20 (see FIG. 10). The swing base 170 is coupled to the coil support 155, as well as the central portion of the swing base 170 is coupled via an appropriate member to the second collimator 20.

When a current flows in a given direction (hereinafter referred to as the "forward direction"), the coil support 155 moves to the right in FIG. 11 due to the magnetic field created by the magnets 165 and Fleming's left-hand rule. When a current flows in the direction opposite to the given direction (hereinafter referred to as the "reverse direction"), the coil support 155 moves to the left in FIG. 11. For example, when a current in the reverse direction is supplied to the voice coil motor 150a and a current in the forward direction is supplied to the voice coil motor 150d, the support 155 of the voice coil motor 150a moves to the left while the support 155 of the voice coil motor 150d moves to the right. As a result, the swing base 170 moves upward, while the second collimator 20 swings upward. When a current is passed in the opposite direction, the second collimator 20 swings downward. The similar operations of the voice coil motors 150b and 150c allow the second collimator to swing in directions orthogonal to the plane of the paper. The swing base 170 is coupled to a coupling member disposed on a spherical surface of the first collimator 10 (i.e., coupling member comprising arc-shaped curvilinear-motion bearings 151 of FIG. 10 in two directions so that two degree of freedom can be obtained), so that swinging movements can be performed.

As a feature of the present embodiment, a movable dummy weight 169 is disposed in a hollow portion (SP) in the coil support 155 of the voice coil motor 150. The position of the center of gravity in the swing portion and the moment of inertia are adjusted with the movement of the dummy weight 169 within the hollow portion. Specifically, the moment of inertia is equalized around the reference axes (X-axis and Y-axis) in the coordinates in which the center of the swinging movements is the origin.

The moment of inertia can be adjusted with a higher degree of freedom by disposing the dummy weights 169 in all four voice coil motors 150a to 150d. Alternatively, the dummy weights 169 may be disposed only in the two voice coil motors 150a, 150c driving in the up and down direction which is particularly affected by gravity. Further, when only two of the voice coil motors 150 are used as the swing drive mechanism 25, two dummy voice coil motors may be disposed so that dummy weights are disposed therein.

Figure 12:
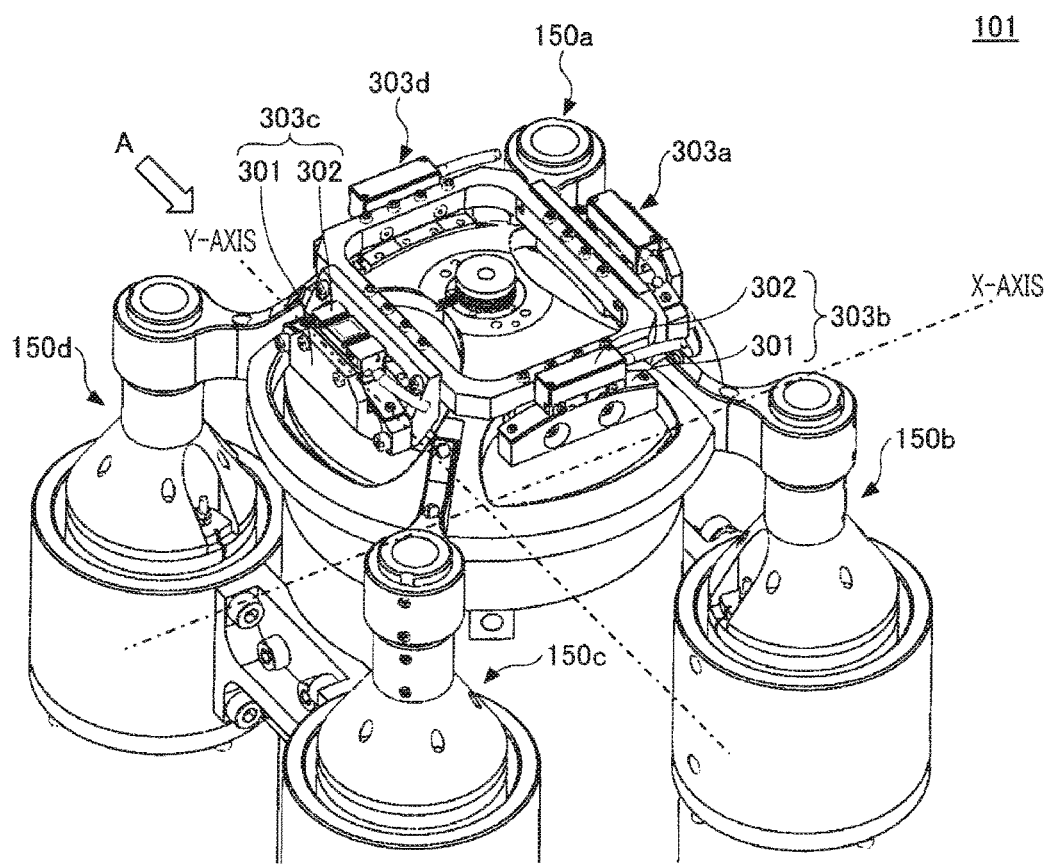
FIG. 12 is a perspective view illustrating another example of a collimator device.

FIG. 12 is a perspective view illustrating another example of the collimator device 101. In this example, as a displacement detection means, i.e., the swing angle detection unit 30, an encoder system is employed instead of an autocollimator system in FIG. 10. Two encoders 303b, 303d are disposed along the X-axis, while two encoders 303a, 303c are disposed along the Y-axis (collectively, referred to as "encoders 303"). The encoders 303 each include an encoder sensor 302 and a linear scale 301.

The encoders 303 include a magnetic encoder, which is excellent in environmental robustness against dust, oil, etc., and a low-cost optical reflective encoder, which can be used where a favorable environment permits. The encoder output types include an incremental type and an absolute type. The incremental type requires determining the origin every time when a power supply is turned on/off. The absolute type does not require such operation since position information is recorded.

The encoders 303 serving as a displacement detection sensor are important in performing drive control, and thus it is preferable to employ redundancy, that is, to dispose them in sets. Thus, two sets of encoders 303 are disposed to detect each of angles (θx, θy) about the X-axis and the Y-axis, thereby providing backup in the event of failure of the sensor or malfunction of the sensor itself. The same type of encoders may be used for two sets of encoders in each axis direction, while the magnetic encoders and the optical encoders may be used in combination.

In the configuration in FIG. 12, the voice coil motors 150a to 150d are disposed such that the drive axes thereof are tilted at 45 degrees with respect to the X-axis and Y-axis serving as references. In terms of layout, the drive axes of the voice coil motors are set at 45 degrees relative to the reference axes, so that the arrangement of the encoders 303a to 303d are facilitated and the collimator device 101 is downsized.

However, the drive axes of the voice coil motors 150a to 150d may be aligned with the X-axis and Y-axis which are the references. In this case, the drive axes of the voice coil motors 150a to 150d are parallel to the orientation of the encoders 303a to 303d, which simplifies position-to-angle conversion, resulting in enhanced control accuracy.

The point of intersection of the X-axis and Y-axis constituting reference coordinates is the location of the target 4, which is the X-ray source, and also the rotational center of the swinging movement of the swing portion configured with the second collimator 20 and components mounted thereto. As described above, the location of the target 4 serving as the rotational center is aligned with the center of gravity of the swing portion.

Figure 13:
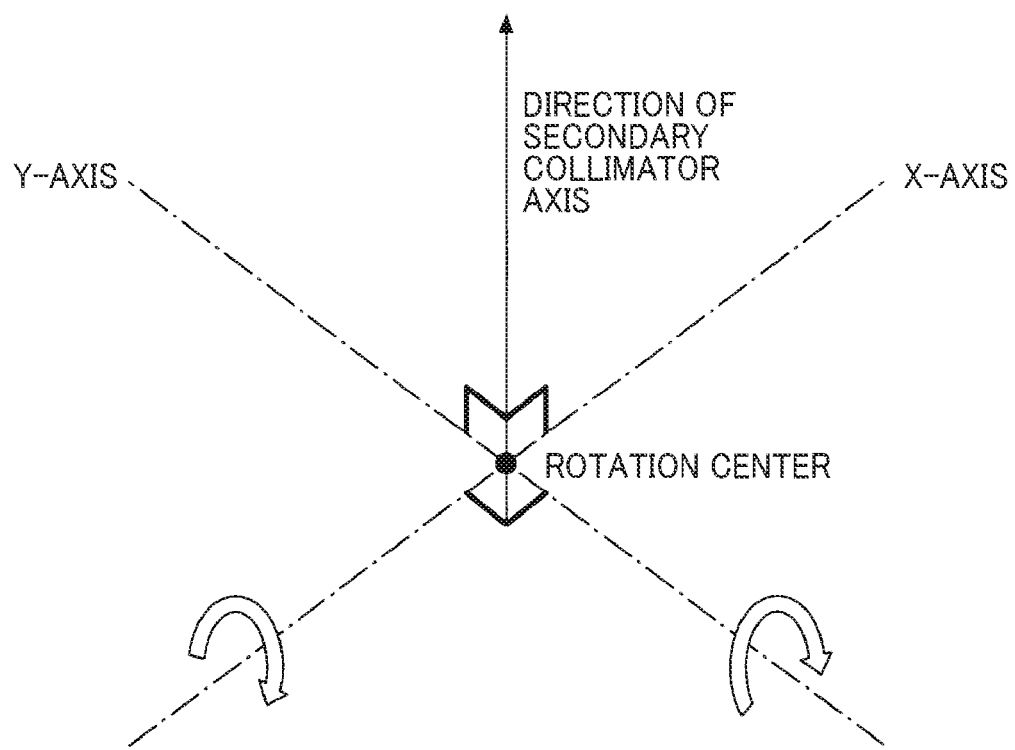
FIG. 13 is a diagram illustrating an X-axis and a Y-axis serving as rotational axes of a swinging movement.

FIG. 13 is a diagram illustrating the X-axis and Y-axis serving as the rotation axes of the swinging movements of the second collimator 20. The point of intersection of the X-axis and Y-axis is the location of the target, which is the X-ray source, and the rotational center about which the second collimator 20 is swung in two directions orthogonal to each other. The moment of inertia of the components of the swing portion, configured with the second collimator and the components mounted thereto, is substantially equal about each of the X-axis and the Y-axis, which are the reference axes in two directions orthogonal to each other passing through the rotational center of the swinging movement. With such an arrangement, the effects caused by imbalance in inertia can be cancelled using the main parts of speed-FF-control parameters. As a result, tracking performance can be stabilized against acceleration and deceleration of the target (affected area).

Figure 14:
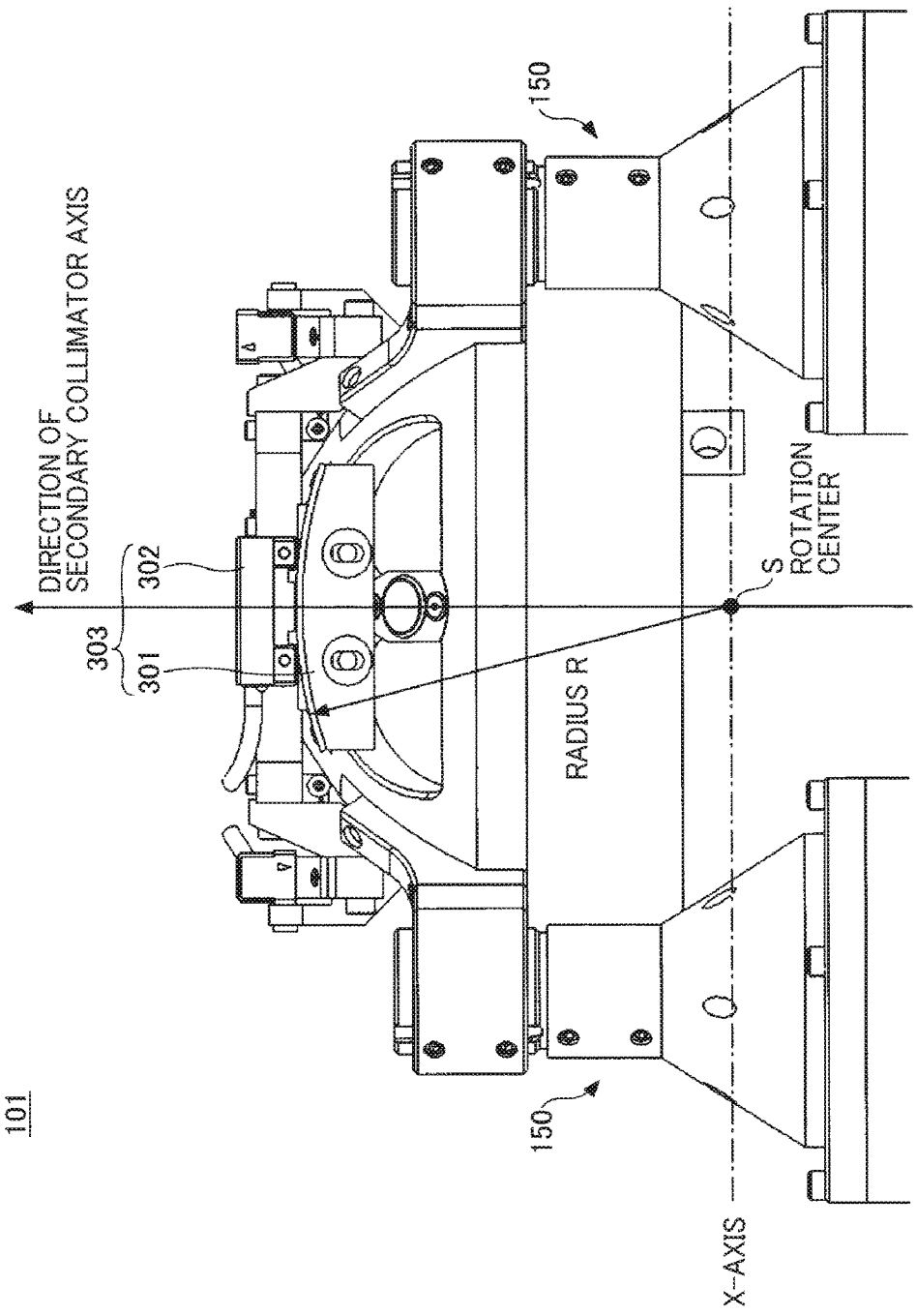
FIG. 14 is a side view illustrating a collimator device.

FIG. 14 is a side view illustrating the collimator device 101. The linear scale 301 of the encoder 303 is mounted as an arc of a curve having a radius R with respect to the X-axis and Y-axis passing through the center point of the swinging movement. FIG. 14 illustrates the encoder 303 mounted as an arc relative to the X-axis. The encoder sensor 302 is disposed at a location opposed to an arc-shaped scaler surface of the linear scale 301, and moves along an arc while maintaining a certain distance from the fixed linear scale 301. Position information read from the encoder 303 is easily substituted by angle information. The relation between a resolution (unit distance dx) of the encoder 303, a basic swing angle $d\theta$, a radius R of a curve is given as $dx=R*d\theta$. When the magnetic linear scale 301 is used, a width of the scale is set to a value considering a range of the swinging movements orthogonal to each other, using a rubberized magnet having a certain flexibility and a north pole and a south pole disposed at a pitch of several millimeters, for example. *

With the above-described mechanical mechanism, when dynamic tracking irradiation is performed while the X-ray head 100 is continuously moved, stable radiation can be performed with accuracy.

Third Embodiment

In a third embodiment, the third solution, i.e., drive control based on mechanical elements is provided. Specifically, parameters for mechanical elements relating to the swinging movements are reflected in the speed FF control. A speed FF gain is set using the inertia value assuming uniform arrangement of the moment of inertia. Thus, the effects of an imbalance in the moment of inertia emerge as a speed FF output, which causes variation in output and deterioration in tracking accuracy. Therefore, a configuration in which speed FF control is stably performed even if a change in mechanical element occurs is provided.

Figure 15:
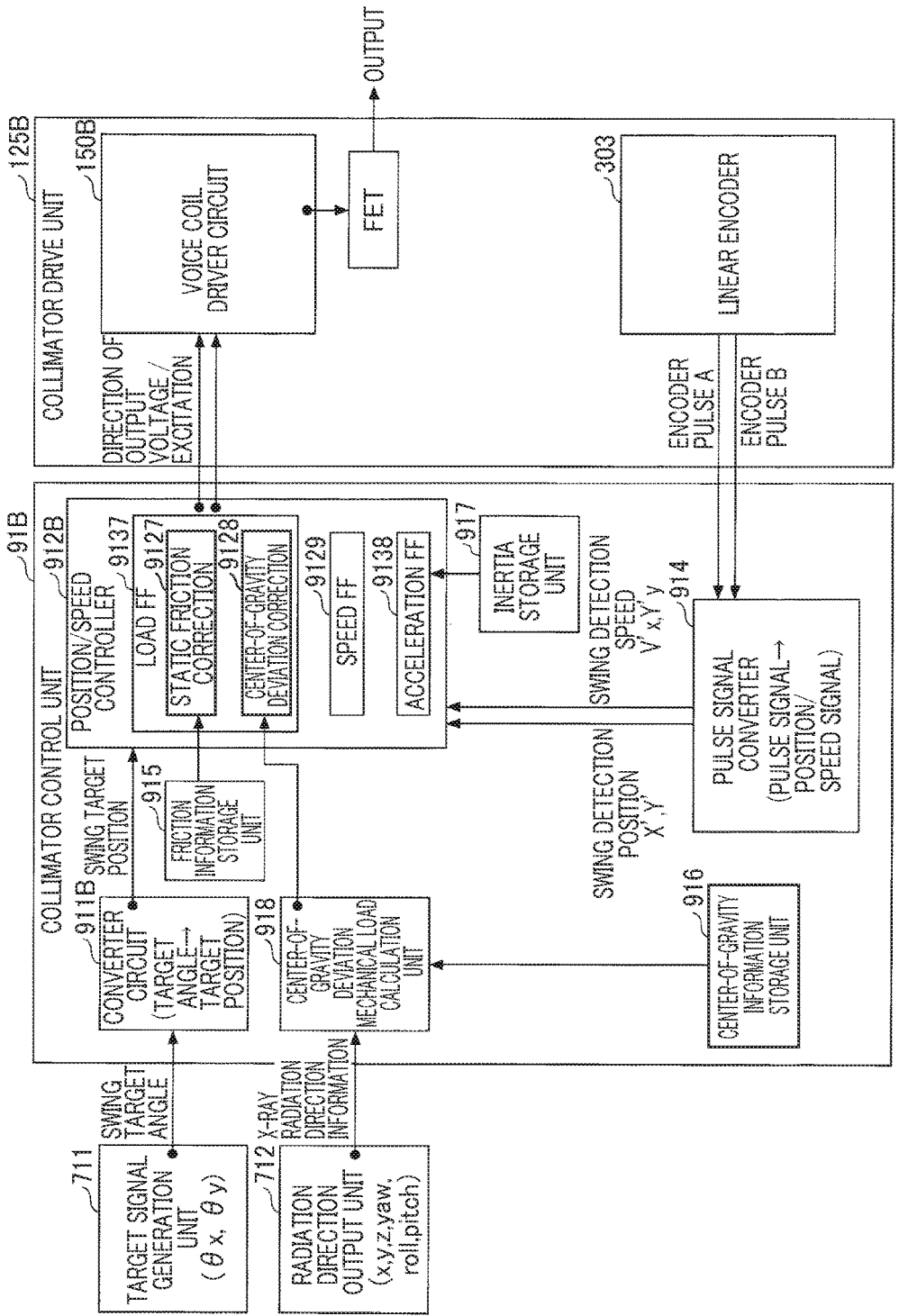
FIG. 15 is a block diagram illustrating a control system configured to perform drive control of a collimator device.

FIG. 15 a block diagram illustrating a control system according to the third embodiment that is configured to perform drive control of the collimator device 101. The same components as those in FIG. 8 are designated as the same reference numerals, and the descriptions thereof are omitted. The drive control system includes the target signal generation unit 711, a radiation direction output unit 712, a collimator control unit 91B, and a collimator drive unit 125B. The target signal generation unit 711 and the radiation direction output unit 712 are implemented by the tracking controller 71. The collimator control unit 91B is included in the controller 90 in the X-ray head 100. The collimator drive unit 125B includes a voice coil driver circuit 150B and a linear encoder 303.

The collimator control unit 91B comprises a converter circuit 911B, a position/speed controller 912B, the pulse signal converter 914, a friction information storage unit 915, the center-of-gravity information storage unit 916, an inertia storage unit 917, and the center-of-gravity deviation mechanical load calculation unit 918.

The target signals ($\theta x$, $\theta y$) indicative of the swing angle of the target are inputted from the target signal generation unit 711 via the sub-unit controller 80 (see FIG. 7) to the converter circuit 911B. The converter circuit 911 is configured to convert the inputted target signal into target position (X, Y), and output swing target position information to the position/speed controller 912B.

The position and direction of the X-ray head 100, i.e., the coordinate information (x, y, z, yaw, roll, pitch) of the six-axis manipulator 200, are inputted from the radiation direction output unit 712, via the sub-unit controller 80, to the center-of-gravity deviation mechanical load calculation unit 918, as X-ray emission direction information. Since gravity applied to the swing portion varies with the positions and directions of the X-ray head 100, its mechanical load also varies. The center-of-gravity deviation mechanical load calculation unit 918 is configured to calculate a mechanical load caused by the center of gravity deviation, based on the inputted of X-ray emission direction information and the center-of-gravity information recorded in the center-of-gravity information storage unit 916, and such calculation result is outputted to the position/speed controller 912B. The center-of-gravity information may include distance information indicative of the center of gravity deviation from the swing pivot (rotational center) of the collimator device 101 and the magnitude of the load caused by the center of gravity deviation.

On the other hand, from the linear encoder 303 of the collimator drive unit 125B, encoder pulses A, B for obtaining current angle information on the second collimator 20 are inputted to the pulse signal converter 914. The pulse signal A, and pulse signal B are a pair of signals having phases deviating from each other by 90°. The pulse signal converter 914 is configured to transform angle information indicated by the inputted pulse signals A, B into a swing detection position (X', Y') and a swing detection speed (V'x, V'y), and supply such transform results to the position/speed controller 912B.

The position/speed controller 912B comprises a load FF calculation unit 9137, a speed FF calculation unit 9129, and an acceleration FF calculation unit 9138. The load FF calculation unit 9137 includes a static friction correction unit 9127 and the center-of-gravity deviation correction unit 9128. The static friction correction unit 9127 is configured to read static friction information from the friction information storage unit 915, and set a static friction correction value. In the friction information, dynamic friction may be included. The static friction correction value includes such an upper threshold value as to act only when a target speed is zero or in the vicinity thereof. For example, when the motion of the lung tumor changes in direction, the position deviation when the dynamic friction is generated is reduced from the static friction that is generated when the swing collimator has zero speed, so that irradiation accuracy is improved.

The static friction is dependent on speed, and thus can be reflected in load FF control. These methods may be employed: a method of rendering a target speed, obtained by differentiating the target position, zero and further adding a fixed gain until a given threshold value is exceeded; and a correction method of rendering a detection speed zero and further adding a fixed gain until a given threshold value is exceeded may be employed. The fixed gain is a gain corresponding to the maximum static friction force.

The center-of-gravity deviation correction unit 9128 is configured to calculate the center-of-gravity deviation correction value for correcting a load variation based on the mechanical load inputted from the center-of-gravity deviation mechanical load calculation unit 918. The acceleration FF calculation unit 9138 is configured to read inertia information from the inertia storage unit 917, and set acceleration FF value.

The position/speed controller 912B is configured to generate a drive signal using at least a part of the static friction correction value, the center-of-gravity deviation correction value, a speed FF value, and the acceleration FF value, in addition to the target position (X, Y), the detection position (X', Y'), and the detection speed (V'x, V'y), and output the drive signal to the voice coil driver circuit 150B. The center-of-gravity information and inertia information vary depending on the radiation direction of the X-ray head 100 operated by the six-axis manipulator 200. Thus, based on the radiation direction, the drive signal for cancelling a load caused by the gravity is supplied to the voice coil driver circuit 150B. In this drive signal, the output voltage of the voice coil driver circuit 150B and the direction of excitation are defined.

The friction information storage unit 915, the center-of-gravity information storage unit 916, and the inertia storage unit 917 in the collimator control unit 91B may be implemented by memory of the controller 90 in the X-ray head 100. Alternatively, they may be implemented by memory of a controller in the control device 120 of the radiation therapy system 1000. When the converter circuit 911B, the position/speed controller 912B, the center-of-gravity deviation mechanical load calculation unit 918, and the pulse signal converter 914 of the collimator control unit 91B are implemented by the functions of software, a drive control program stored in the memory of the controller 90 may be executed by a processor.

In setting FF parameters in the position/speed controller 912B, friction variation and gain variation may be learned and reflected in FF value.

Figure 16:
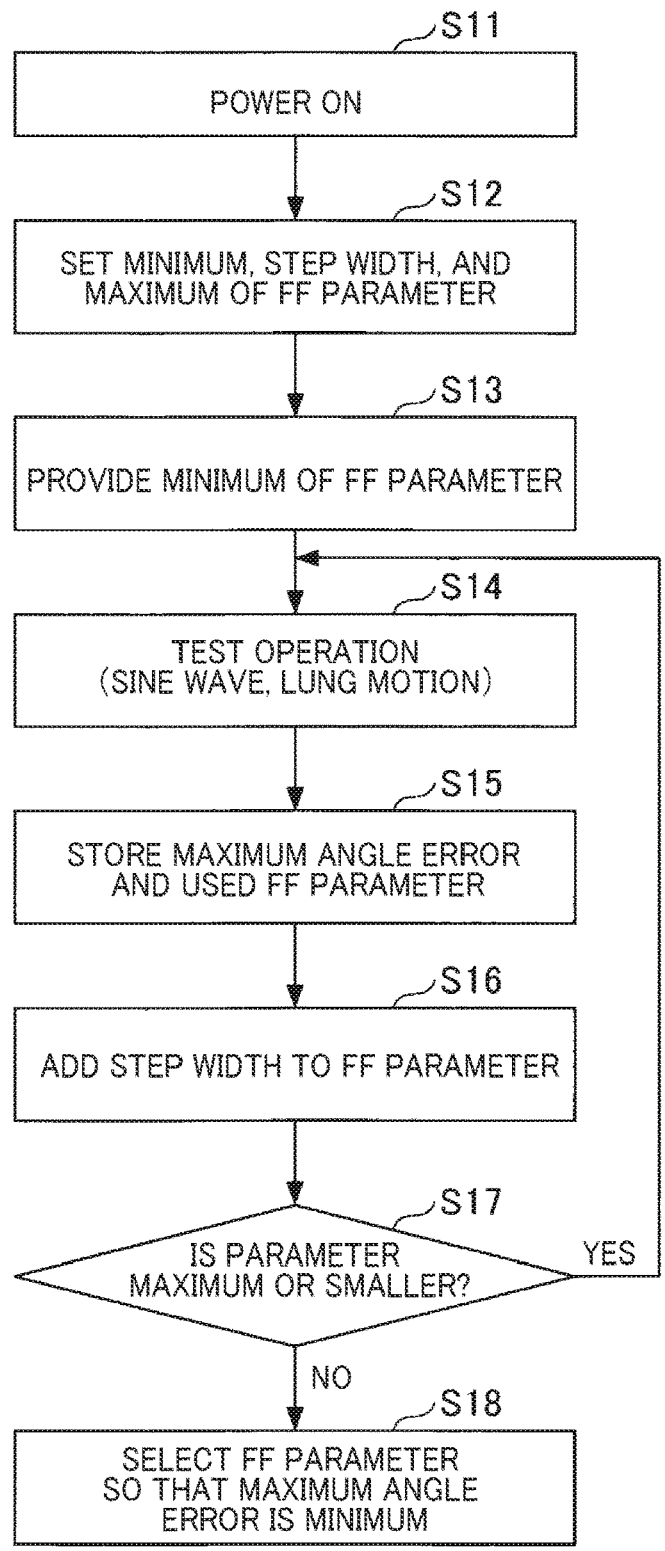
FIG. 16 is a flow chart illustrating feedforward (FF) reflecting friction variations.

FIG. 16 is a flow chart in which friction variation is learned and reflected in feedforward (FF) control. Inertia mass, friction force (static friction), and FF gain are assumed as parameters used for FF control. The inertia mass is determined by each component, and such a value is used. The friction force and FF gain are determined through the following procedure, illustrated in the flow chart of FIG. 16.

First, in step S11, a power supply of a swing collimator system is activated (S11).

Next, in step S12, the minimum value, a step width, and the maximum value of each of the static friction and FF gain used for FF control (S12) are set. The range of each of the parameters of the static friction and FF gain is determined by the minimum value and the maximum value.

Then, in step S13, input the set the minimum values of each of the static friction and FF gain to the position/speed controller 912B are input (S13).

Thereafter, in step S14, a test operation such as sine wave operation or a typical lung motion is performed (S14).

Subsequently, in step S15, the static friction value set in the position/speed controller 912B and the maximum value of an error between target angle (θx, θy) and detection angle (θ' x, θ' y) during test operation (S15) are stored.

Subsequently, in step S16, a predetermined step width is added to each of the parameters that are set for FF control (S16), and in step S17 it is determined whether such parameter is equal to or smaller than the maximum value (whether it is within the set range) or not (S17). When the parameter is equal to or smaller than the set maximum value (YES at S17), the process returns to step S14 and repeat steps S14 to S17. When the parameter is greater than the maximum value (NO at S17), the parameter when the stored maximum angle error is the minimum is used for FF control, after which control terminates.

FIG. 17 illustrates a specific example of the parameters for FF control. The flow chart in FIG. 16 is specifically explained with reference to FIG. 17. When setting the ranges of parameters and the step sizes at S12, regarding the static friction, the minimum value is set to 1 [N·m·s/rad], the maximum value is set to 5 [N·m·s/rad], and a step width is set to 1 [N·m·s/rad]. Further, regarding the FF gain, the minimum value is set to 0.5, the maximum value is set to 0.9, and a step width is set to 0.1.

The first to fifth rounds, a friction value that is substituted in FF control of the position/speed controller 912B, is sequentially increased with a step size of 1 [N·m·s/rad]. At this time, the FF gain is fixed (e.g., 0.5). The value of 3 [N·m·s/rad], at which the maximum angle error is the smallest, is selected in the predetermined range of friction (1 [N·m·s/rad] to 5 [N·m·s/rad]).

Next, in the sixth to tenth rounds, the FF gain is sequentially increased. At this time, the friction is fixed (e.g., 3 [N·m·s/rad]). The FF gain of 0.8, at which the maximum angle error is the smallest, is selected in the predetermined range of FF gain (0.5 to 0.9).

Based on this learning function, the friction information held in the friction information storage unit 915 may be updated on a regular basis. With the friction information being updated, it is possible to implement FF control that greatly reduces spot position error, even if there is variation with time in friction force, and/or change due to part replacement, repair, and/or the like.

Figure 18A:
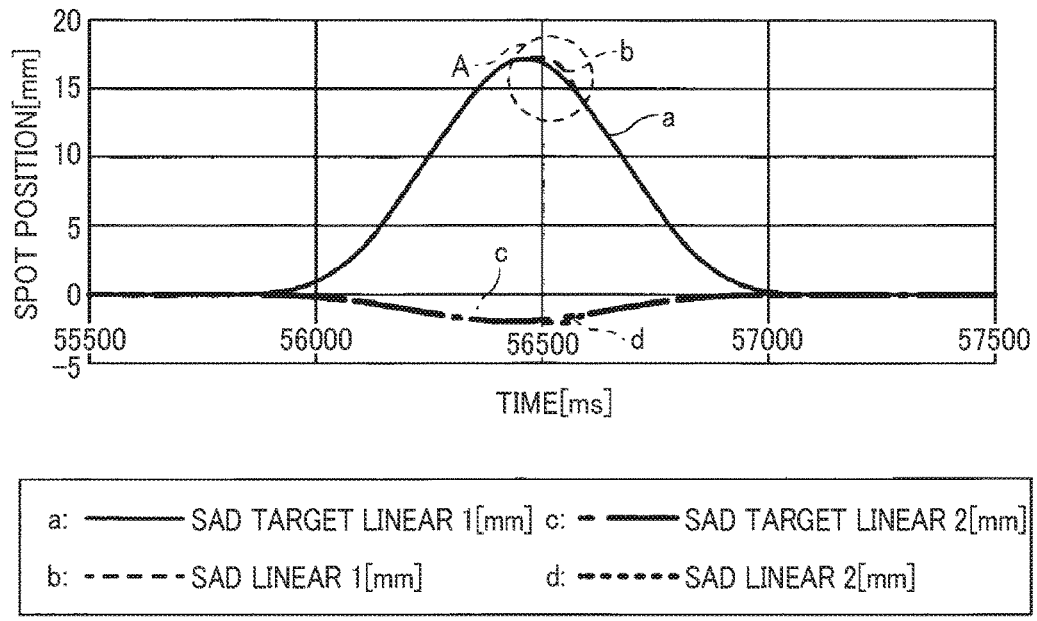
FIGS. 18A and 18B are diagrams illustrating grounds for correcting tracking using FF control.
Figure 20A:
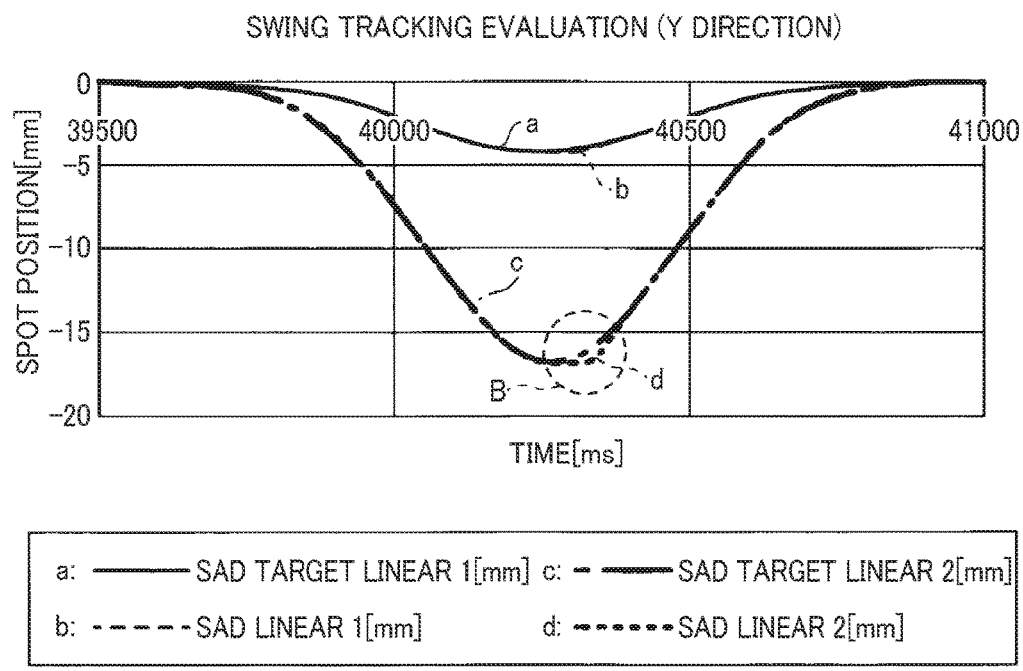
FIGS. 20A and 20B are diagrams illustrating grounds for correcting tracking using FF control.
Figure 20B:
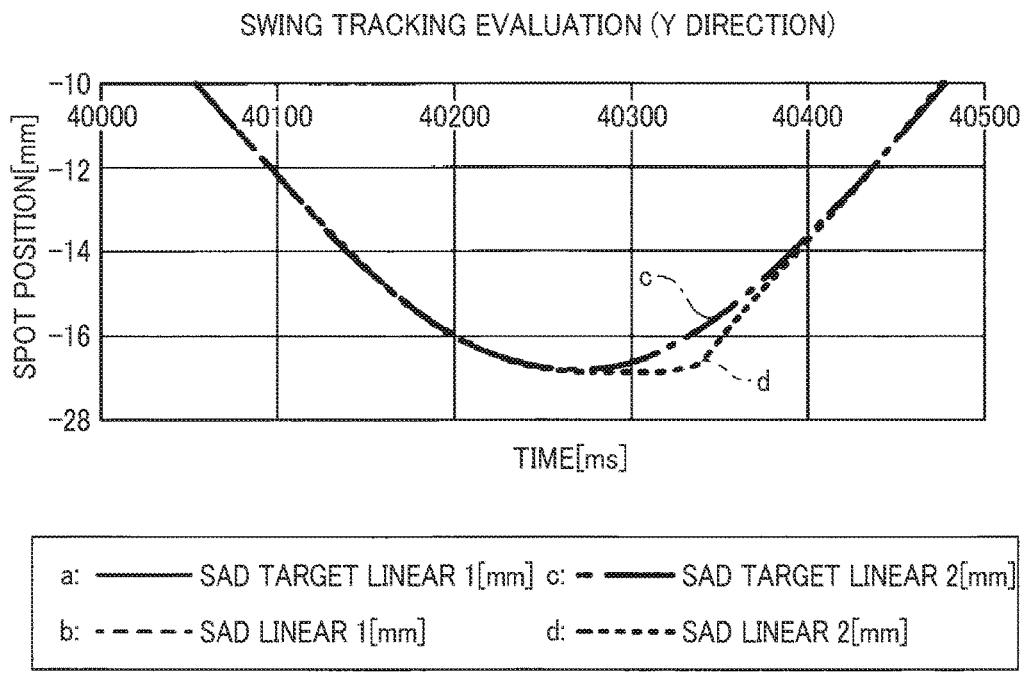
Figure 21:
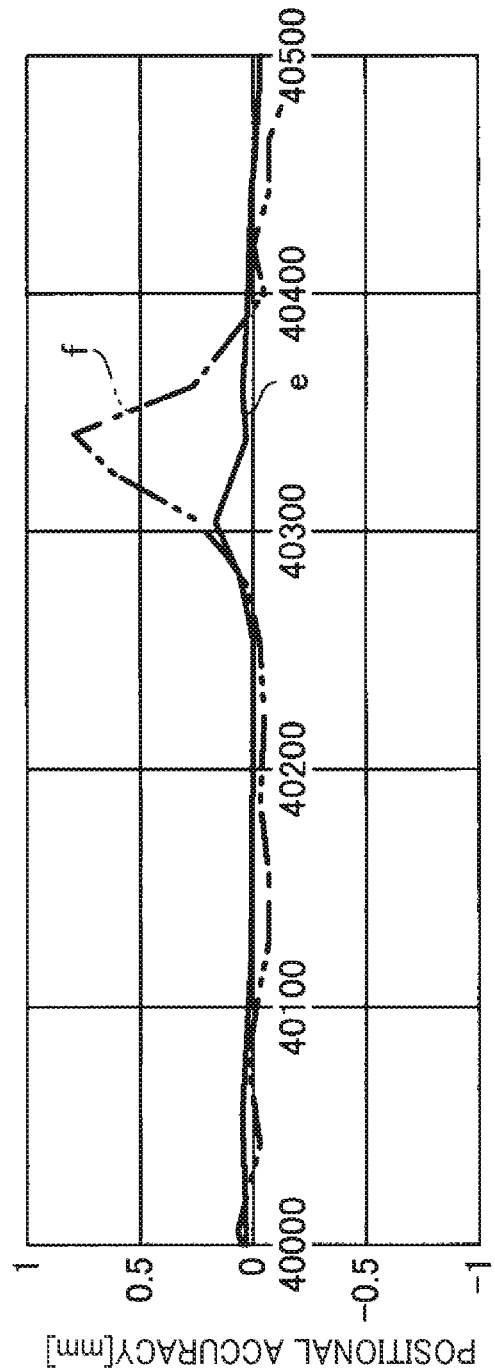
FIG. 21 is a diagram illustrating grounds for correcting tracking using FF control.

FIGS. 18A to 21 are diagrams illustrating grounds for enhancing tracking performance using FF control. FIGS. 18A-B and 19 illustrate tracking performance evaluation and positional accuracy in the X-direction, while FIGS. 20A-B and 21 illustrate tracking performance evaluation and positional accuracy in the Y-direction. These measurement results are acquired without using FF control based on mechanical elements.

Figure 18B:
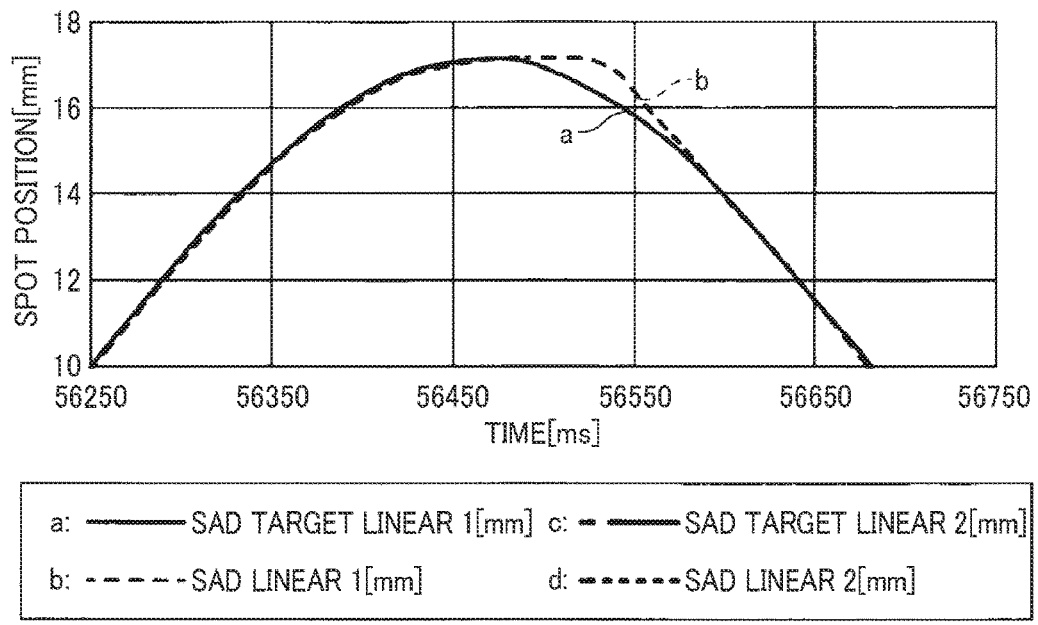

In FIGS. 18A-B, a line a indicates a target spot position based on the detection result of a linear encoder 1 configured to detect change in angle about the X-axis, while a line b indicates an actual spot position. A line c indicates a target spot position based on the detection result of a linear encoder 2 configured to detect change in angle about the Y-axis, while a line d indicates an actual spot position. In FIG. 18A, although the line c is substantially aligned with the line d, a deviation indicated with a circle A occurs between the line a and the line b. FIG. 18B is an enlarged view of the circle A. The actual spot position deviates from the target spot position by about 1 mm. Such deviation is considered to be caused by variation in friction in a sliding unit such as bearings in the collimator device 101 and/or unevenness in inertia about the axes of swinging movements.

Consequently, as illustrated in FIG. 19, in the positional accuracy with respect to the linear encoder 2, an error falls within a range of 0.3 mm or smaller. Whereas, in the positional accuracy with respect to the linear encoder 1, an error increases up to 0.7 mm.

In contrast, in the Y-direction, as in FIG. 20A, a line a is substantially aligned with a line b, while a deviation indicated with a circle B occurs between a line c and a line d. FIG. 20B is an enlarged view of the circle B. The actual spot position deviates from the target spot position by about 1 mm.

Consequently, as illustrated in FIG. 21, in the positional accuracy with respect to the linear encoder 1, an error falls within a range of 0.2 mm or smaller. Whereas, in the positional accuracy with respect to the linear encoder 2, an error increases up to 0.8 mm.

In order to reduce these errors, in the third embodiment, the friction and the FF gain that minimize the maximum angle error are selected by the method illustrated in FIGS. 16 and 17, to perform drive control involving friction correction and the center of gravity deviation correction. Accordingly, tracking radiation is performed with higher accuracy while deviation between the target spot position and the actual spot position is minimized. It is presupposed also in the third embodiment, similarly to the second embodiment, that the moment of inertia of the components in the swing portion is arranged substantially uniform about each of the X-axis and the Y-axis. However, by reflecting inertia information in FF control, it is possible to reduce position deviation during acceleration/deceleration.

Further, as can be understood from FIGS. 18A to 21, the friction or the effects of the friction may vary between in the X-direction and in the Y-direction in the reference coordinates. Thus, parameters for performing FF control may be determined separately between in the X-direction and in the Y-direction.

Other Embodiments

Figure 22A:
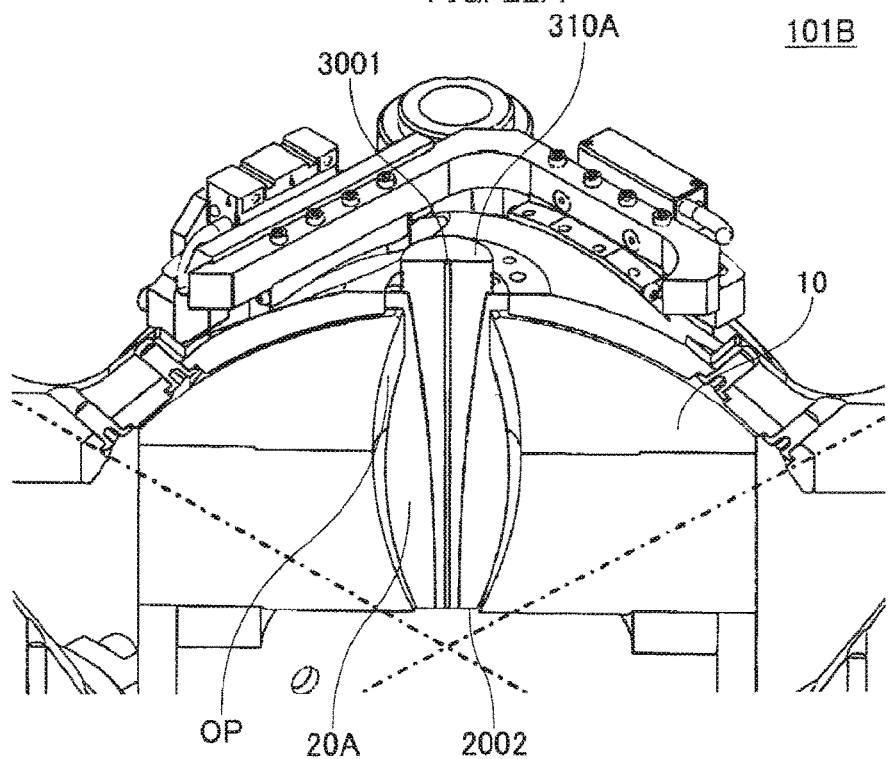
FIGS. 22A and 22B are diagrams illustrating an example using a third collimator.
Figure 22B:
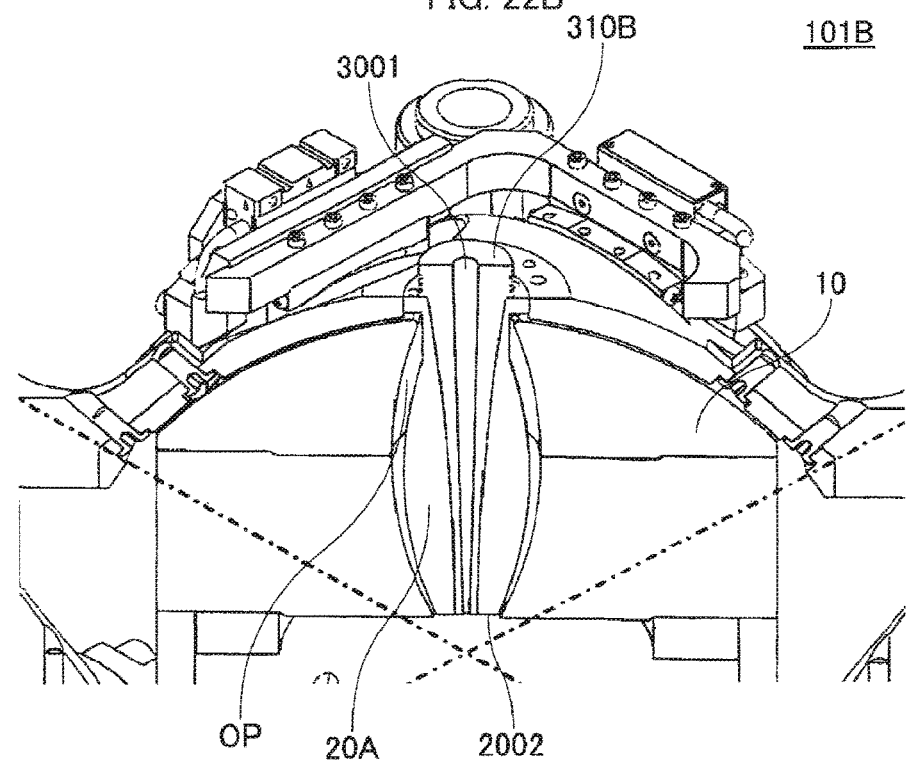

FIGS. 22A and 22B illustrate another embodiment. In FIGS. 22A-B, a third collimator 310A (310B) having a different radiation field is used in addition to the second collimator 20A. The third collimator 310A (310B) is interchangeably inserted within the second collimator 20A, so that the radiation field can be changed. It may be desirable to narrow the diameter of the emitting X-ray beam, depending on the position and size of the affected area. Further, it is desirable to be able to appropriately select and change the diameter of the beam, depending on the position and size of the affected area. The third collimator 310 enables such adjustments of the radiation field.

The second collimator 20A has a shape capable of accommodating the third collimator 310A (310B) as well as swinging within the first collimator 10. As an example, the second collimator 20A has a gently curved outer wall, and implements a smooth swing in a gap OP and stable X-ray shielding.

The third collimator 310A in FIG. 22A and a third collimator 310B in FIG. 22B have the same external shape, but has different diameters of collimator spaces 3001. The collimator space 3001 in FIG. 22A has a diameter smaller than that of the collimator space 3001 in FIG. 22B, and is capable of further narrowing an X-ray emitting beam. The third collimator 310A or 310B is interchangeably inserted within the second collimator 20A, thereby being able to obtain a desired beam diameter.

The third collimator 310A, 310B is inserted to an output end 2002 of the second collimator 20A, and swings integrally with the second collimator 20A. With this configuration, the radiation field can be simply changed without disturbing the swinging movement of the second collimator 20A.

In cases where the third collimator is not used, such a configuration is also possible that the multiple second collimators 20 having different radiation fields are prepared so that the second collimators 20 are rendered interchangeable.

Change in shape of the radiation field of the second collimator 20 causes change in mass from the rotational center, resulting in change in inertia value. Since the center of gravity in the swing portion also deviates, inertia further increases when the dummy weight 169 for adjustment is used. Since there are many devices installed in the collimator device 101, a means for supporting such change in inertia is required. To address this, inertia information on the second collimator 20 or information on a drive target model based on the inertia information is stored in memory of the controller 90, so that such information can be reflected in acceleration FF control.

When causing the X-ray head 100 to perform drive control of a collimator, a drive control program may be stored in memory, to cause a processor to execute the drive control program.

Finally, features and effects of the present disclosure will be simply described.

(1) The feedforward control of acceleration and/or load in the X-ray radiation device is performed using the parameter related to the mechanical characteristics stored in the storage unit, thereby implementing collimator drive control with less position error during tracking.

(2) The center-of-gravity information on the swing portion in the collimator device 101 is stored in the storage unit, so that the center-of-gravity information is reflected in collimator drive control. This restrains variation in friction force caused by the effects of gravity, even if the collimator changes in posture according to the irradiation in multiple directions.

(3) The rotational center of the swinging movements of the swing portion in the collimator device 101 is aligned with the center of gravity of the swing portion. This restrains variation in friction force caused by the effects of gravity to the minimum, even if the collimator changes in posture according to the irradiation in multiple directions.

(4) Inertia information is stored in the storage unit, to be reflected in FF control of drive of the collimator. This reduces position error during acceleration/deceleration.

(5) The moment of inertia of the components in the swing portion is arranged substantially uniform about the X-axis and the Y-axis, which are the reference axes orthogonal to each other passing through the rotational center of the swinging movements. This cancels the effects of variation in mechanical inertia constituting acceleration FF gain. Accordingly, tracking performance can be stabilized against the target changing with acceleration/deceleration.

(6) Static friction information is stored in the storage unit, to be reflected in collimator drive control. As a result, when the motion of a lung tumor changes in direction or the like, the position error when the dynamic friction is generated is reduced from the static friction that is generated when the swing collimator has zero speed, so that higher irradiation accuracy is obtained.

(7) Dynamic friction information is stored in the storage unit, to be reflected in collimator drive control. This enhances tracking performance of control and reduces position error in spot irradiation position.

(8) Parameters for creating feedforward information are determined separately between in the X-axis and in Y-axis in the reference coordinates, so that optimal FF control is performed in each of the directions even through characteristics in friction are different between the directions.

(9) Drive axes of the drive mechanism(s) are aligned with the X-axis and Y-axis, which are the reference coordinate axes, and the sliding directions of the sliding parts are arranged to be parallel to the X-axis and Y-axis, so that smooth drive is implemented.

(10) The drive axes of the drive mechanism(s) are aligned with the X-axis and Y-axis, which are the reference coordinate axes, and the detection directions of the position detection means (encoders) are rendered parallel to the X-axis and Y-axis, so that control calculation is facilitated.

(11) The mechanism(s) (dummy weight, etc.) for adjusting the moment of inertia about the X-axis and Y-axis and the center of gravity of the swing portion are provided. This further enhances the effects of minimizing variation in friction force caused by the effects of gravity.

(12) With the use of the voice coil motor(s) for the drive mechanism(s), the mechanical mechanism and the drive unit are directly coupled to enhance stiffness, so that control with higher precision is enabled.

(13) With the use of the encoders for the displacement detection means, miniaturization, low cost, and stabilization in the apparatus are secured.

(14) With the use of the curved sliding members (bearings) orthogonal to each other as sliding parts, smooth drive is implemented.

The present disclosure can widely be utilized for non-destructive testing devices for structures and the like and dynamic tracking sensors, in addition to radiation therapy for a patient having an affected area in a complex shape. The X-ray radiation device and collimator drive control according to embodiments of the present disclosure can be applied to treatment devices using not only X-ray irradiation but also laser beam irradiation and neutron irradiation, dynamic tracking non-destructive tests and sensors.

The above-described embodiments are illustrative and do not limit this disclosure. Thus, numerous additional modifications and variations are possible in light of the above teachings. For example, elements or features of different illustrative and embodiments herein may be combined with or substituted for each other within the scope of this disclosure and the appended claims. Further, features of components of the embodiments, such as number, position, and shape, are not limited to those of the disclosed embodiments and thus may be set as preferred. Further, the above-described steps are not limited to the order disclosed herein. It is therefore to be understood that, within the scope of the appended claims, this disclosure may be practiced otherwise than as specifically described herein.

What is claimed is:

1. A radiation emitting apparatus, comprising:
a radiation source to generate radiation;
a first collimator to define a maximum radiation field of the radiation;
a second collimator to regulate the radiation field and direction of irradiation, the second collimator disposed within the first collimator;
a swing portion, incorporating the second collimator, that swings in two directions orthogonal to each other, the swing portion having a rotational center and a center of gravity;
a displacement detector to detect displacement of the second collimator relative to a reference point;
a drive mechanism operatively connected to the swing portion to drive the swing portion;
a control unit operatively connected to the drive mechanism to generate feedforward control information to control the drive mechanism; and
a storage unit included in the control unit to store one or more parameters related to mechanical movement of the swing portion,
the control unit generating feedforward control information based on an inputted target swing angle, a detected displacement, and the one or more parameters stored in the storage unit, and outputting a drive signal containing the feedforward control information to the drive mechanism.

2. The radiation emitting apparatus according to claim 1, wherein the storage unit stores center-of-gravity information on the swing portion, and
the control unit calculates a center-of-gravity deviation correction value based on radiation direction information and the center-of-gravity information, and includes the center-of-gravity deviation correction value in the feedforward control information.

3. The radiation emitting apparatus according to claim 1, wherein a rotational center of the swing portion is substantially aligned with a center of gravity of the swing portion.

4. The radiation emitting apparatus according to claim 1, wherein the storage unit stores one of drive-target-model information and inertia information on the second collimator and/or the swing portion, and
the control unit generates the feedforward control information using the inertia information or the drive-target-model information.

5. The radiation emitting apparatus according to claim 4, further comprising a third collimator capable of forming a radiation field different from the second collimator, wherein
the storage unit further stores inertia information on the second collimator and the third collimator, and
the control unit generates the feedforward control information using the drive-target-model information or the inertia information for the second collimator and the third collimator.

6. The radiation emitting apparatus according to claim 1, wherein moment of inertia of the swing portion is substantially equalized about an X-axis and a Y-axis,
the X-axis and Y-axis being reference axes in the two directions orthogonal to each other passing through the rotational center of the swing portion.

7. The radiation emitting apparatus according to claim 1, wherein the storage unit stores static friction information, and
the control unit generates a static-friction-correction value based on the static friction information, and includes the static-friction-correction value in the drive signal.

8. The radiation emitting apparatus according to claim 1, wherein the storage unit stores dynamic-friction information, and
the control unit generates the feedforward control information based on the dynamic-friction information.

9. The radiation emitting apparatus according to claim 1, wherein the one or more parameters used to generate the feedforward control information are determined separately for each of the reference axes in the two directions orthogonal to each other passing through the rotational center of the swing portion.

10. The radiation emitting apparatus according to claim 1, wherein drive axes of the drive mechanism are aligned with the X-axis and the Y-axis, and
the swing portion includes a first sliding part that slides in a direction parallel to the X-axis, and a second sliding part that slides in a direction parallel to the Y-axis.

11. The radiation emitting apparatus according to claim 1, wherein the drive axes of the drive mechanism are aligned with the X-axis and the Y-axis, and
the displacement detector includes a pair of detection units parallel in direction of detection to the X-axis, and another pair of detection units parallel in direction of detection to the Y-axis.

12. The radiation emitting apparatus according to claim 1, wherein the drive mechanism includes a dummy weight to adjust the moment of inertia and position of the center of gravity of the swing portion.

13. The radiation emitting apparatus according to claim 1, wherein the control unit generates the feedforward control information based on the inputted target swing angle, the detected displacement, and the one or more parameters stored in the storage unit, and
the one or more parameters includes a friction value at which an error between the target swing angle and a detection angle is at a minimum and a feedforward control gain is at a maximum,
wherein the drive signal is generated based on the friction value.

14. A radiation therapy apparatus, comprising:
a manipulator including an arm movable about n axes (where n is 6 or more); and
an X-ray head connected to an end of the arm,
the X-ray head including:
    an X-ray source,
    a first collimator to define a maximum radiation field of X-rays,
    a second collimator to regulate the radiation field and a direction of irradiation, the second collimator disposed, with a gap, within the first collimator,
    a swing portion to perform a swinging movement in two directions orthogonal to each other, together with the second collimator, the swing portion including the second collimator,
    a displacement detector to detect a displacement relative to a reference point of the second collimator,
    a drive mechanism to drive the swing portion,
    a control unit to control the drive mechanism, and
    a storage unit to store a parameter related to a mechanical movement of the swing portion,
the control unit generating feedforward control information based on an inputted target swing angle, the detected displacement, and the parameter stored in the storage unit, and outputting a drive signal containing the feedforward control information to the drive mechanism.

15. A collimator drive control method for a radiation emitting apparatus including a radiation source to generate radiation; a first collimator to define a maximum radiation field and emission direction of the radiation; a second collimator to regulate the radiation field and a direction of irradiation, the second collimator disposed within the first collimator; a swing portion to perform a swinging movement in two directions orthogonal to each other together with the second collimator, the swing portion including the second collimator; a displacement detector to detect displacement of the second collimator relative to a reference point; a drive mechanism to drive the swing portion; and a storage unit to store one or more parameters related to mechanical movement of the swing portion,
the method comprising:
receiving inputted target swing angle information at the control unit;
obtaining the displacement from the displacement detector;
reading the parameter from the storage unit;
generating, with the control unit, feedforward control information based on the target swing angle information, the displacement, and the one or more parameters stored in the storage unit; and
outputting, from the control unit, a drive signal containing the feedforward control information to the drive mechanism to drive the swing portion.

* * * * *